US012770416B2

(12) United States Patent
Stern et al.

(10) Patent No.: US 12,770,416 B2
(45) Date of Patent: Oct. 20, 2026

(54) AUTOMATED SYSTEM FOR IMAGING, IDENTIFICATION, AND ISOLATION OF ORGANOIDS

(71) Applicant: Cell Microsystems, Inc., Durham, NC (US)

(72) Inventors: Rachel Allysa Stern, Rougemont, NC (US); Jessica Kessler Hartman, Cary, NC (US); Steven Charles Gebhart, Durham, NC (US); Caleb Macrae Fleming, Cary, NC (US); Brandon Thompson, Durham, NC (US); Keith Williams, Durham, NC (US); Robert W. Mcclellan, Apex, NC (US)

(73) Assignee: Cell Microsystems, Inc., Durham, NC (US)

( * ) Notice: Subject to any disclaimer, the term of this patent is extended or adjusted under 35 U.S.C. 154(b) by 247 days.

(21) Appl. No.: 18/619,874

(22) Filed: Mar. 28, 2024

(65) Prior Publication Data

US 2024/0320992 A1 Sep. 26, 2024

Related U.S. Application Data

(63) Continuation of application No. 18/686,511, filed as application No. PCT/US2022/041886 on Aug. 29, 2022.

(Continued)

(51) Int. Cl.
*G06V 20/69* (2022.01)
*C12M 1/32* (2006.01)

(Continued)

(52) U.S. Cl.
CPC ........... *G06V 20/698* (2022.01); *C12M 23/12* (2013.01); *C12M 41/12* (2013.01); *C12M 41/36* (2013.01);

(Continued)

(58) Field of Classification Search
CPC .. G06V 20/698; G06V 20/695; G06V 20/693; G06T 7/162; G06T 7/11;

(Continued)

(56) References Cited

U.S. PATENT DOCUMENTS

2018/0246099 A1 8/2018 Kotton
2019/0256817 A1 * 8/2019 Gebhart ............ G01N 15/0612

(Continued)

FOREIGN PATENT DOCUMENTS

WO 2018097950 A1 5/2018

OTHER PUBLICATIONS

International Search Report for Application No. PCT/US22/41886 dated Jan. 25, 2023.

(Continued)

*Primary Examiner* — Ming Shui
(74) *Attorney, Agent, or Firm* — KDW FIRM PLLC

(57) ABSTRACT

A microwell array specifically designed for culturing organoids is provided along with a system to enable automated imaging, identification, and isolation of individual organoids. The microwells of the microarray include a releasable cellraft that enables the automated release and transfer of selected organoids present on the cellrafts to a separate collection plate. Organoids grown on the microarray can be reliably tracked, imaged, and phenotypically analyzed by the instrument system in brightfield and fluorescence as they grow over time, then released and transferred fully intact for use in downstream applications. The use of the system is demonstrated using mouse hepatic and pancreatic organoids for single-organoid imaging, clonal organoid generation, parent organoid subcloning, and single-organoid RNA extraction for downstream gene expression or transcriptomic analysis.

19 Claims, 33 Drawing Sheets

Related U.S. Application Data

(60) Provisional application No. 63/280,224, filed on Nov. 17, 2021, provisional application No. 63/237,781, filed on Aug. 27, 2021.

(51) Int. Cl.

| | |
|---|---|
| ***C12M 1/34*** | (2006.01) |
| ***C12M 1/36*** | (2006.01) |
| ***G06T 7/00*** | (2017.01) |
| ***G06T 7/11*** | (2017.01) |
| ***G06T 7/162*** | (2017.01) |

(52) U.S. Cl.
CPC ........... *C12M 41/48* (2013.01); *G06T 7/0012* (2013.01); *G06T 7/11* (2017.01); *G06T 7/162* (2017.01); *G06V 20/693* (2022.01); *G06V 20/695* (2022.01); *G06T 2200/24* (2013.01); *G06T 2207/10024* (2013.01); *G06T 2207/10064* (2013.01); *G06T 2207/20072* (2013.01); *G06T 2207/30024* (2013.01)

(58) Field of Classification Search
CPC ............... G06T 7/0012; G06T 2200/24; G06T 2207/10024; G06T 2207/10064; G06T 2207/20072; G06T 2207/30024; C12M 41/12; C12M 41/36; C12M 41/48
See application file for complete search history.

(56) References Cited

U.S. PATENT DOCUMENTS

2019/0355119 A1* 11/2019 Hu .......................... G06T 7/136
2020/0010797 A1 1/2020 Hoehnel

OTHER PUBLICATIONS

Williamson, Ian et al, "A High-Throughput Organoid Microinjection Platform to Study Gastrointestinal Microbiota and Luminal Physiology," Cellular and Molecular Gastroenterlogy and Hepatology, 2018.

Gracz et al., "A high-throughput platform for stem cell niche co-cultures and downstream gene expression analysis," Nature Cell Biology, vol. 17, No. 3: 340-349 (Feb. 2015)—Abstract.

Kakni et al., "Intestinal Organoid Culture in Polymer Film-Based microwell Arrays," advanced Biosystems, vol. 4, Issue 10: 1-12 (Oct. 2020).

Extended European Search Report in EP Application No. 22862173.6 dated Jun. 13, 2025, 10 pages.

* cited by examiner

AUTOMATED SYSTEM FOR IMAGING, IDENTIFICATION, AND ISOLATION OF ORGANOIDS

CROSS-REFERENCE TO RELATED APPLICATIONS

This application is a continuation of U.S. patent application Ser. No. 18/686,511 filed on Feb. 26, 2024, which is a 371 of International Application No. PCT/US2022/041886 filed on Aug. 29, 2022, which claims benefit of and priority to U.S. Provisional Patent Application Ser. No. 63/237,781 filed Aug. 27, 2021 and U.S. Provisional Patent Application Ser. No. 63/280,224 filed Nov. 17, 2021, the disclosure of which is incorporated herein by reference in its entirety.

STATEMENT REGARDING FEDERALLY SPONSORED RESEARCH

This invention was made with government support under grant number 5R44ES032782 awarded by the National Institutes of Health. The government has certain rights in the invention.

BACKGROUND

For decades, two-dimensional (2D) cell culture models have been used to study disease and advance drug development, as cell lines are typically inexpensive and easy to culture, making them convenient for high-throughput analysis. However, establishing cell lines, which are often derived from tumors or immortalized, involves extensive genetic and phenotypic adaptation to the culture environment, which decreases their relevance to normal cells and ultimately reduces their applicability as a model system. In addition, 2D models lack important spatial arrangement and cell-to-matrix interactions, further limiting their predictive power. This lack of translation of 2D cell culture models to in vivo outcomes significantly impacts the drug discovery pipeline, where the probability of success has been estimated at only 13.8%. While 2D models continue to provide significant value in research and development programs, there is considerable need for more advanced cellular models that provide better physiological relevance to tissues and organs.

There are several three-dimensional (3D) models that offer increased complexity, and subsequent physiological relevance, over 2D models, including co-cultures, spheroids, encapsulated cells, and organoids. Organoids are self-organizing three-dimensional (3D) structures that are grown from embryonic stem cells, induced pluripotent stem cells (iPSCs), or adult stem cells from humans and animal models alike. Organoids derived from adult stem cells, which are organ-constrained, and pluripotent stem cells (PSCs) have seemingly infinite expansion potential; and when the organoids are differentiated, they exhibit tissue-specific physiological and diseased states that make them a more relevant and attractive in vitro model than 2D single cell type monolayer cultures for developmental research, drug discovery, personalized medicine, and toxicological studies.

For 3D assembly, organoids require a source of extracellular matrix (ECM) to serve as a basement membrane. There are several commercially available basement membrane extract products, with Matrigel being one of the most commonly used. Traditional culture methods of organoids involve cells propagated between layers of or embedded in Matrigel domes. These culture methods are highly effective in supporting organoid assembly and growth but present several challenges in accurate assessment and throughput. First, standard culture methods result in a random arrangement of organoids in all three dimensions, with multiple structures per well that are frequently overlapping. This increases the number of focal planes needed to capture the population and requires advanced instrumentation and computational methods for complex 3D image-based analysis to resolve and assess each organoid. In addition, while the source materials for organoids are heterogeneous, which is advantageous in capturing the diversity of in vivo cellular material, traditional culture methods fail to capture the heterogeneity since responses are often homogenized across the population within each well. For these reasons, there is a need for new culture techniques and automated instrumentation that can more efficiently and accurately evaluate heterogenous organoid populations through single-organoid imaging and recovery. Newer consumable technologies have been developed that focus on multiple microwell positions that house individual organoids in standard tissue culture consumable formats; however, these technologies still require extensive, manual upstream effort and do not offer retrieval capabilities. Some recent technologies have leveraged image-guided aspiration for retrieval of individual 3D structures, but these tools have their own shortcomings—such as involving physical manipulation forces that can disturb the structure of organoids—that limit their utility to destructive endpoint analysis.

One instrument system that enables high throughput imaging and retrieval of single cells in 2D cell culture is the CellRaft AIR System (Cell Microsystems, Inc., Durham, NC) and see also, for example, PCT patent application publication no. WO 2018/097950. The CellRaft AIR System is a hardware and software system with a cell culture consumable designed for 2D adherent cell culture that enables automated identification and isolation of single cells. The CellRaft AIR System utilizes a microwell array comprising a formed, elastomeric grid of indentations or "wells", where the wells contain a releasable, optically transparent, microfabricated element, referred to as a "cell-raft". These microarrays enable the isolation of cells in a viable and unperturbed state, while simultaneously providing a culture environment that replicates standard in vitro conditions in tissue culture dishes. The micron-sized cell-rafts in the microarrays used in the CellRaft AIR System have a size of 100×100 μm or 200×200 μm with three reservoir layouts having the cellrafts in either a single reservoir, 4 separate reservoirs, or 24 separate reservoirs. While the microarrays facilitate growth of a wide range of adherent and suspension cell types, the growth area for organoids on the largest 200×200 μm cellraft format is limited. In the CellRaft AIR System, a cell sample of interest is seeded on the microwell array where the cells randomly distribute into microwells following a Poisson-like distribution. After imaging and identification, individual cells of interest can be isolated through a stress-free methodology that utilizes mechanical forces to release the chosen cellraft from its microwell without disturbing the attached cell layer and gently transfers it to a 96-well tissue culture or PCR plate using a magnetic wand. The process for release of 100 μm and 200 μm cellrafts from their microwells and collection to a separate plate has been validated to success rate of >95%. However, organoids are large structures grown in extracellular matrix rather than in liquid culture like 2D cells, and this presents challenges to the automated culture, image analysis, and collection of organoids.

Therefore, current methods for culture and analysis of organoids face bottlenecks in accurate assessment and throughput. The present disclosure provides a system for automated, high throughput assembly, growth, image analysis, and isolation of organoids.

SUMMARY

In one embodiment of the present invention, an automated method is provided for culturing, monitoring, and retrieving organoids. The method includes loading an organoid fragment suspension or a single cell suspension in a cell culture media that includes a dilute extracellular matrix (ECM) at a temperature below the polymerization point of the ECM into the microwells of a microarray. The microwells of the microarray include a releasable, paramagnetic cellraft at the bottom of the microwell and the organoid fragments or single cells settle onto the surface of the cellrafts. The method includes placing the microarray at a temperature sufficient to cause the ECM to polymerize, and the organoid fragments or single cells become loosely attached to the cellrafts as a result of the ECM polymerization. The organoid fragments or single cells are cultured for a desired period to enable the formation of organoids. The method includes mounting, at one or more times, the microarray onto an instrument assembly of a system. The instrument assembly includes a microscope objective having a lens and an optical axis, a motorized release needle, and a motorized magnetic collection wand. The needle and the wand are aligned with the microscope optical axis. The system comprises: i) an imaging device that includes the microscope objective and that is configured for obtaining images of the forming or formed organoids on the cellrafts within the microwells of the microarray, ii) an actuator that is configured for controlling the instrument assembly to release a selected cellraft having an organoid of interest from the microwell, and iii) a computer system that includes at least one processor and memory, the computer system programmed for automated imaging of the forming or formed organoids and release and transfer of the selected cellraft having the organoid of interest to a collection plate. The system affects the automated imaging and release and transfer by: acquiring one or more images of the forming or formed organoids on the cellrafts within the microwells of the microarray, including in a z-axis, using the imaging device, identifying, by analyzing the one or more images, one or more selected cellrafts, and controlling the actuator to release the selected cellraft from the microarray by controlling the release needle to apply pushing energy to a surface opposite the microwell comprising the selected cellraft, and to deposit the released cellraft into a mapped location of a collection plate by controlling the magnetic collection wand. The method includes instructing, at one or more times, through a user interface with the computer system, the acquisition of one or more images of the forming or formed organoids on the cellrafts and the deposit of at least one selected cellraft having the organoid of interest into the collection plate.

In some embodiments, the collection plate is a U-bottom 96-well plate, PCR collection plate, or PCR tube.

The microwells of the microarray, are at least about 75 μm deep, have a width of at least about 400 μm, have cellrafts of at least about 400×400 μm, and are separated by walls having an average width of at least about 25 μm. In one embodiment, the microwells of the microarray are about 80 μm deep, have a width of about 500 μm, have cellrafts of about 500×500 μm, and are separated by walls having an average width of about 30 μm. The microarray can include 46×46 of the microwells in a single reservoir for the cell culture media.

In one embodiment, the selected cellrafts are transferred to the collection plate at 90% efficiency.

In some embodiments, the ECM is Matrigel, UltiMatrix, Basement Membrane Extract Type II, or other matrices purified from animal-derived sources. The dilute ECM can include an ECM diluted to a final concentration of about 2%, 3%, 4%, 5%, 10%, 20%, or 30% or the dilute ECM can range from about 0.24, 0.36, 0.48, 0.6, 1.2, 2.4, or about 3.6 mg/ml total protein.

In one embodiment, the ECM is a xeno-free synthetic hydrogel, not derived from animal sources. The dilute hydrogel can range from about 0.24, 0.36, 0.48, 0.6, 1.2, 2.4, or about 3.6 mg/ml total protein.

The microarray can be mounted onto the instrument assembly of the system for imaging and/or release and transfer of one or more selected cellrafts containing an organoid of interest at one or more times including, but not limited to, 1 day, 2 days, 3 days, 4 days, 5 days, 6 days, 7 days, 2 weeks, 3 weeks, or 4 weeks, or more.

The automated method can include instructing, at one or more times, through a user interface with the computer system a calculation of one or both of diameter and other phenotypic parameters of the forming or formed organoids in the microarray.

The automated method can include exporting one or more of the acquired images, wherein the acquired images include one or more z-stack images acquired in the z-axis.

In some embodiments, one or more clonal organoids having a diameter ranging from 200 μm to 1 mm are formed in the microarray by culturing for the desired period of time a single cell of the single cell suspension loaded into one or more of the microwells.

In some embodiments, the organoid fragment suspension or the single cell suspension loaded into the microarray comprises a gene edit or a gene mutation. The gene edit can be a CRISPR edit. The single cell suspension can be from a patient derived cell or tissue. The patient derived cell or tissue can have a known mutation.

In one embodiment, the organoid fragment suspension is generated from a parent organoid, and the parent organoid is subcloned by culturing for the desired period of time one or more single fragments of the organoid fragment suspension in one or more of the microwells and instructing the acquisition of one or more images of the forming or formed organoids on the cellrafts and the deposit of at least one selected cellraft having the organoid of interest into the collection plate.

In one embodiment, the organoid of interest deposited into the collection plate is derived from a single cell of the single cell suspension loaded into the microarray, and the method further includes dissociating the deposited organoid of interest into an organoid fragment suspension and repeating the steps of loading, placing, mounting, and instructing to form and deposit one or more child organoids of interest into the collection plate. The organoid of interest and the one or more child organoids of interest can contain a gene edit or a known mutation.

In some embodiments, the single cell of the single cell suspension contains a gene edit or a known mutation and each of the deposited organoids of interest have the gene edit or the known mutation. The gene edit can be a CRISPR edit.

In some embodiments, the method further includes screening the forming or formed organoids for response to a drug or a molecule for a functional response.

In some embodiments, the method further includes extracting RNA from one or more of the forming or formed organoids for downstream gene expression or transcriptomic analysis.

DETAILED DESCRIPTION

Figure 1A:
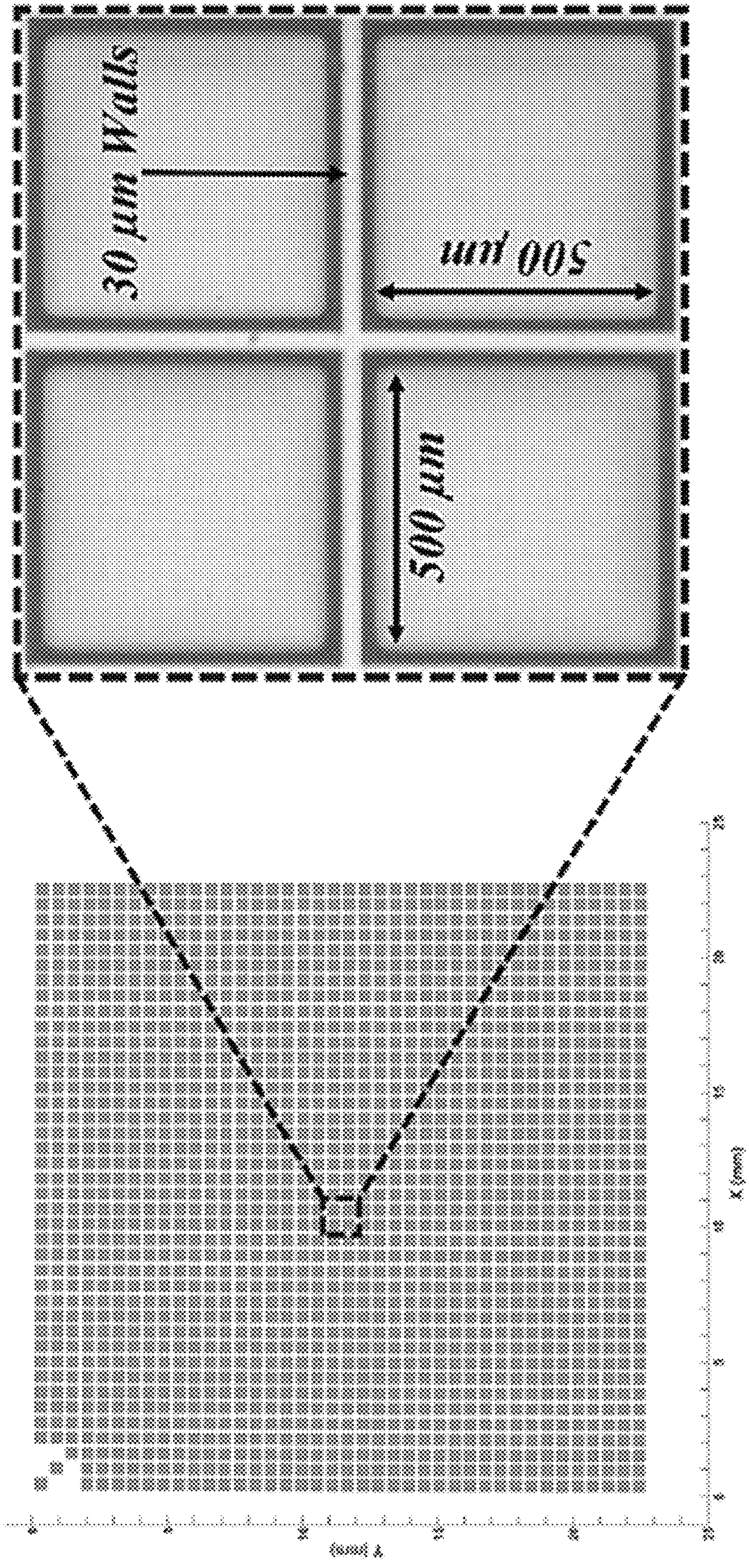
FIG. 1A is an illustration of an example three-dimensional microwell array of the invention, where each microwell comprises a releasable cellraft for culturing and retrieval of organoids showing layout and dimensions of individual cellrafts and PDMS walls.

Embodiments of the present invention now will be described more fully hereinafter with reference to the accompanying drawings, in which embodiments of the invention are shown. This invention may, however, be embodied in many different forms and should not be construed as limited to the embodiments set forth herein. Terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" or "comprising," when used in this specification, specify the presence of stated features, steps, operations, elements, or components, but do not preclude the presence or addition of one or more other features, steps, operations, elements, components, or groups thereof. Additionally, comparative, quantitative terms such as "above", "below", "less", "more", are intended to encompass the concept of equality, thus, "less" can mean not only "less" in the strictest mathematical sense, but also, "less than or equal to."

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein. It will also be understood that when an element is referred to as being "connected" or "coupled" to another element, it can be directly connected or coupled to the other element or intervening elements may be present.

For the purpose of the specification and claims the terms "microscope optical axis" and "microscope imaging axis" are herein used interchangeably.

Traditional organoid culture methods are inadequate because they are low throughput and ill-suited for single organoid imaging, phenotypic assessment, and isolation from heterogenous organoid populations. In one embodiment the present invention provides a microwell array specifically designed for culturing organoids referred to herein as a "microarray" along with an instrument hardware and software system designed to enable automated imaging, identification, and isolation of individual organoids. The microwells of the microarray include a releasable cellraft that enables the automated release and transfer of selected organoids present on the cellrafts to a separate collection plate. Organoids grown on the microarray can be reliably tracked, imaged, and phenotypically analyzed by the instrument system in brightfield and fluorescence as they grow over time, then released and transferred fully intact for use in downstream applications. The use of the disclosed system is demonstrated using mouse hepatic and mouse pancreatic organoids for single-organoid imaging, clonal organoid generation, parent organoid subcloning, and single-organoid RNA extraction for downstream gene expression or transcriptomic analysis. The results validate the ability of the system to facilitate efficient, user-friendly, and automated workflows broadly applicable to organoid research by overcoming several common bottlenecks: 1) single organoid time-course imaging and phenotypic assessment, 2) establishment of single cell-derived organoids, and 3) isolation and retrieval of single organoids for downstream applications.

Embodiments of the present invention fulfill an unmet need for automated tools that are specialized for culture, imaging-based evaluation, and intact isolation of individual organoids. In the present invention, a system is provided including a microarray consumable that is specifically designed for organoid workflows.

Embodiments of the system of the present invention include a microarray consumable for establishing and tracking large, compartmentalized organoids in culture, software with capabilities for imaging and analysis of 3D organoid structures, and hardware that enables fast and high efficiency single organoid isolation. Extracellular matrix (ECM) culture methods are provided that can facilitate a reliable, user-friendly workflow for the development and evaluation of hundreds of individual organoids on a single microarray culture consumable. Proof-of-principle experiments provided in Examples 1-7 demonstrate the utility of embodiments of the invention for high-quality brightfield and fluorescence imaging and temporal assessment of individual organoids, establishing single-cell derived organoids, and isolating individual organoids for downstream applications, such as subcloning and -omics. These workflows and their endpoints continue to increase in prevalence and value in developmental biology, drug discovery, personalized medicine, and toxicology, demonstrating the broad potential of these methods and systems to advance organoid research.

The utility of organoids in bridging the gap between traditional 2D in vitro assays and clinical applications is clear due to their ability to recapitulate key aspects of in vivo organs. However, traditional methods of organoid culture present challenges in throughput, phenotypic assessment via imaging, and recovery of intact, viable organoids for downstream expansion and analysis. The system of the present invention can fill the unmet needs of organoid workflows by enabling user-friendly organoid protocols that offer greater throughput, temporal image acquisition, and data cataloging of individual organoids, while also providing automated isolation and transfer of individual organoids to a collection plate.

To that end, the presently disclosed system includes a microarray tissue culture consumable that can support large organoid growth and hardware and software that can allow for more advanced 3D phenotypic characterization and decision-based automated isolation. In addition, methods are provided that can be widely applicable for using organoids or other 3D culture models in research and development. The experiments provided herein including in Examples 1-7 have demonstrated the use of the automated system including the microarray for phenotypic characterization of organoids using high-quality brightfield and fluorescent imaging, including z-sectioning, as well as the isolation and transfer of organoids of interest into 96-well tissue culture and PCR plates for downstream growth, expansion, or -omics applications.

The system provided herein is uniquely suited to address the bottlenecks and inefficiencies of using standard consumables for organoid culture, including: 1) the manual manipulation of cellular material in ECM, 2) challenges in image acquisition and analysis due to multiple, overlapping structures per well, and 3) the inability to collect individual organoids of interest for further analysis.

The largest microwell array for use with the CellRaft Air System sold by Cell Microsystems, Inc. has a cellraft size of 200×200 μm. The growth area for organoids on the 200×200 μm cellraft format is limited. Therefore, in one embodiment of the present invention, a microarray is provided having cellrafts of 500×500 μm size to support the growth of 3D structures up to 1 mm in diameter, separated by 30 μm walls to deter nonspecific binding and undesired growth of single cells/organoid fragments off the cellraft (FIG. 1A). The microwells of the microarray having cellrafts 500×500 μm in size have a width of about 500 μm and are at least about 75 μm deep. The microwell array comprises a formed, elastomeric grid of wells, where the wells contain a releasable, optically transparent, microfabricated element, the cellraft. The microarray enables the isolation of organoids in a viable and unperturbed state, while simultaneously providing a culture environment that replicates standard in vitro conditions in tissue culture dishes. An exemplary microarray comprises 46×46 cellrafts of 500×500 μm size in a single reservoir, yielding more than 2,100 cellraft positions for segregated organoid growth and the potential to interrogate, characterize, and recover as many organoids from a single microarray consumable as seeding twenty-two 96-well or six 384-well plates. Fabrication of an exemplary microarray is described in Example 1.

In another embodiment, the microwells of the microarray are at least about 75 μm deep, have a width of at least about 400 μm, have cellrafts of at least about 400×400 μm size and are separated by walls having an average width of at least about 25 μm.

Figure 1B:
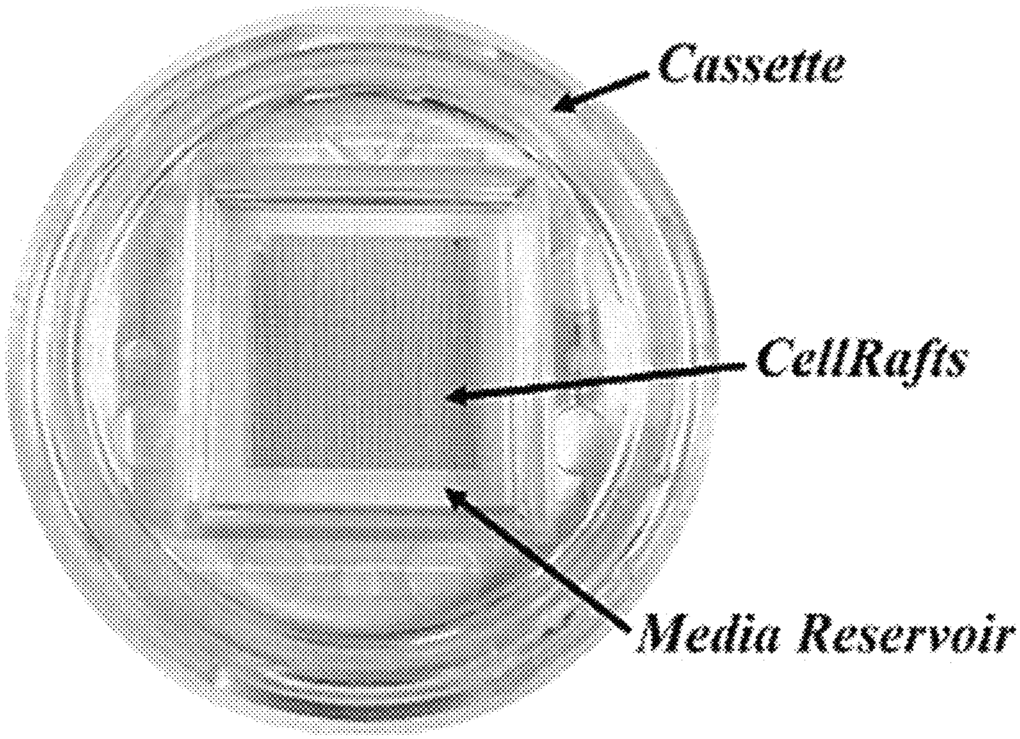
FIG. 1B is an illustration of an example three-dimensional microwell array of the invention, where each microwell comprises a releasable cellraft for culturing and retrieval of organoids showing a fully fabricated microarray.
Figure 1C:
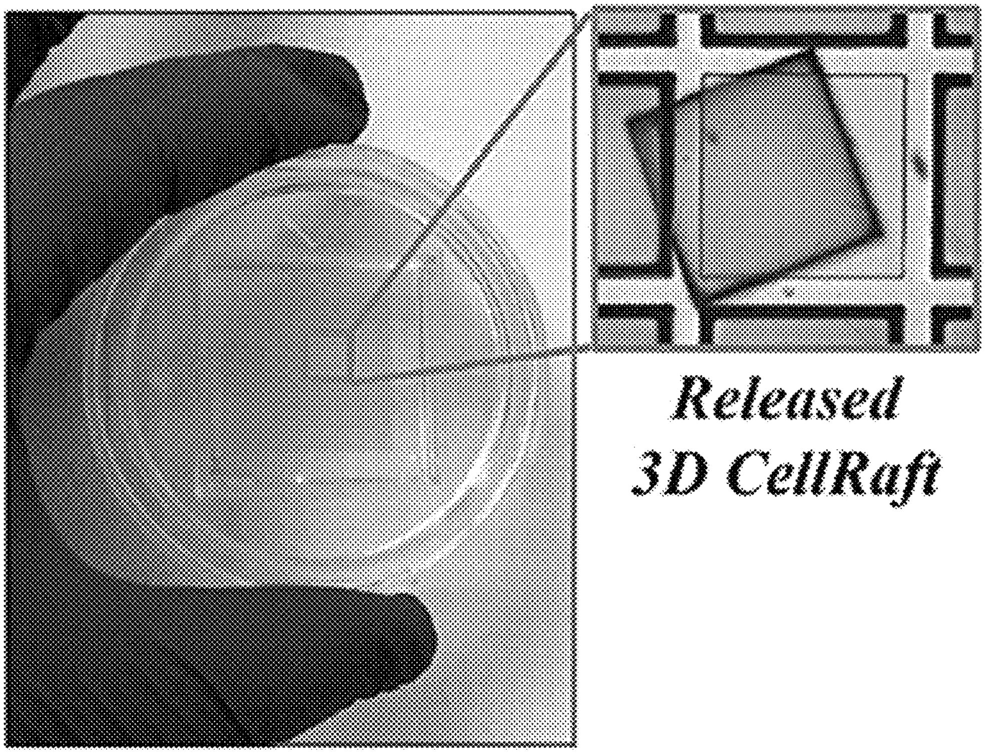
FIG. 1C is an illustration of an example three-dimensional microwell array of the invention, where each microwell comprises a releasable cellraft for culturing and retrieval of organoids showing an image of a cellraft after release from the automated system of the invention.

The microarray can be attached to a polystyrene cassette that provides exterior borders of a contiguous media reservoir that facilitates a highly viable culture environment (FIG. 1B). The polystyrene cassette can be a 65 mm-diameter injection molded polystyrene cassette. When housed in an adapter plate on the instrument hardware of the automated system, each cassette is within ANSI/SLAS tolerance ranges for height, width, and length to ensure compatibility with standard microscopy equipment, liquid handlers, and the automated system. Because establishment of organoids, and organoid assay times, are generally extended compared to 2D culture methods, the present inventors evaluated the integrity of the microarrays after 4 weeks of culture time to mimic use-case scenarios. At the end of the test period, no leaks or structural disruptions nor negative impact on cellraft releasability were observed (FIG. 1C), validating the robustness of the microarray for 3D culture.

In one embodiment, the automated system of invention enables z-stack image acquisition and analysis. In one example, cells are seeded onto the microarray, and the system software, and its companion Off The Air data analysis software (Cell Microsystems, Inc., Durham, NC), provide a user-friendly interface to power the automated imaging, identification, and isolation of organoid-containing cellrafts. While most of the software algorithms and code from the CellRaft AIR System were transferrable to incorporate the larger microarray format, the previous software did not include z-stack imaging functionality desired for 3D workflows, as its original purpose was to scan and image 2D cells attached to the cellraft surface. After performing a standard, single-plane scan of the microarray, the user can now select organoids of interest for z-stack acquisition and specify the slice thickness that the automated system uses as it acquires brightfield and fluorescence images throughout the full height of the selected organoid.

Figure 2A:
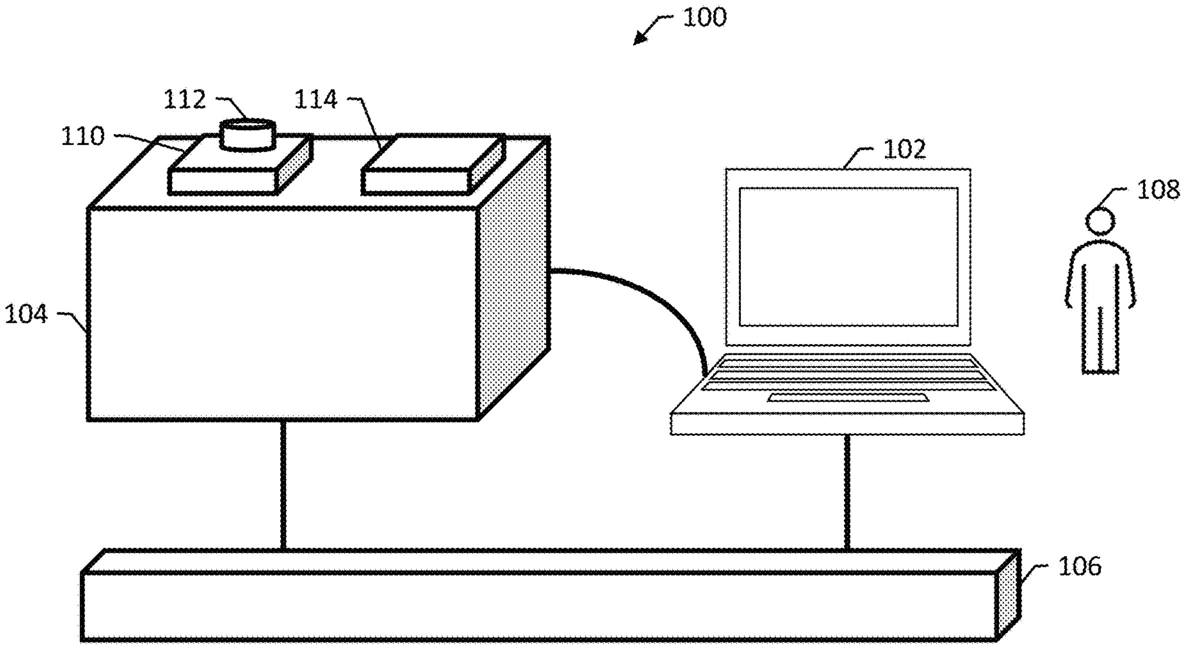
FIG. 2A is an overview diagram of an exemplary system of the invention for imaging and collection of organoids.
Figure 2B:
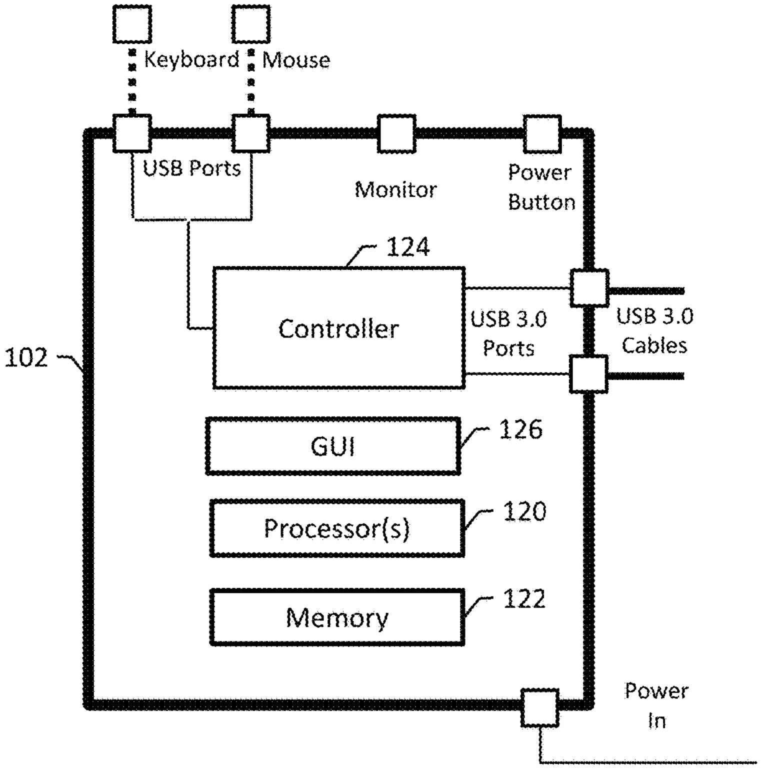
FIG. 2B is a block diagram of the computer system 102 shown in FIG. 2A.
Figure 2C:
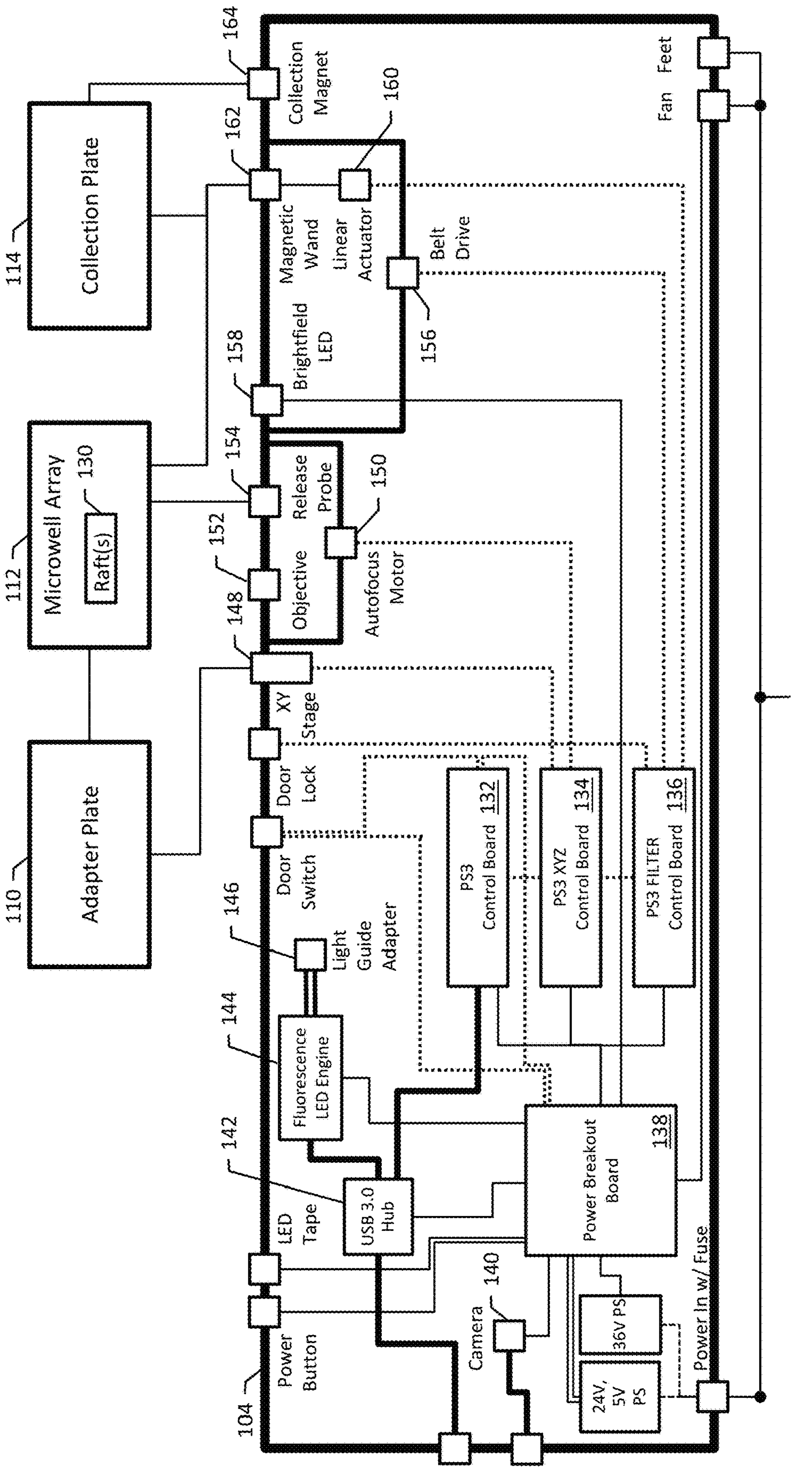
FIG. 2C is a block diagram of the instrument assembly 104 shown in FIG. 2A.

A description of embodiments of the system of the invention is provided with reference to FIGS. 2A-2C and FIGS. 3A-3B. FIGS. 2A-2C are diagrams of an example system 100 for organoid imaging, and collection. The system 100 can be used to identify and collect cellrafts having organoids embedded in extracellular matrix that is loosely attached to the surface of the cellraft. FIG. 2A is an overview diagram of the system 100. The system 100 includes a computer system 102, an instrument assembly 104, an experimental environment 106 (e.g., one or more pieces of laboratory equipment such as power supplies and environmental control systems), and a user 108. The instrument assembly 104 includes an optional adapter plate for receiving a microarray 112 and a collection plate 114 for receiving cellrafts that have been selected and released from the microarray 112. The collection plate 114 can be organized into a standardized format, e.g., as an SBS collection plate. Although a collection plate 114 is shown, the system 100 can alternatively use any appropriate collection structure, such as PCR strip tubes.

Typically, the user 108 would load an organoid fragment suspension or a single cell suspension in a cell culture media comprising a dilute extracellular matrix (ECM) at a temperature below the polymerization point of the ECM into the microwells of a microarray 112 and allow the organoid fragments or cells to settle onto individual cellrafts. After the organoid fragments or cells settle onto the cellrafts, the microarray is placed at a temperature sufficient to cause the ECM to polymerize, and the organoid fragments or single cells become loosely attached to the cellrafts as a result of the ECM polymerization. The organoid fragments or single cells are cultured for a desired period of time to enable organoid formation. The microarray 112 is then placed into the adapter plate 110 of the system 100 for scanning and image analysis. The scanning and image analysis can take place at any number of times over the entire course of the culture period for organoid formation. The user can instruct the system 100 to release a cellraft from the microarray 112 by controlling and using an actuator and to collect the cellraft with the isolated organoid using a magnet. For example, the actuator can be one or more motors configured to move a needle or similar device to release cellrafts. In some examples, the system 100 includes multiple actuators, including, possibly another actuator to move a magnetic wand, and possibly actuators to move a stage, imaging optics, and other mechanical parts of the system.

FIG. 2B is a block diagram of the computer system 102. The computer system 102 includes at least one processor 120, memory 122, a controller 124 implemented as a computer program using the processor 120 and memory 122, and a graphical user interface (GUI) 126. For example, the computer system 102 can be a desktop computer with a monitor and keyboard and mouse, or the computer system 102 can be a laptop or tablet computer or any other appropriate device. The computer system 102 is operatively coupled to the instrument assembly 104, e.g., by universal serial bus (USB) cables.

The controller 124 is programmed for obtaining one or more images of the forming or formed organoids on the cellrafts within the microarray 112; identifying, by analyzing the images, a selected cellraft having a forming or formed organoid of interest; and controlling the instrument assembly 104 to release the selected cellraft carrying the forming or formed organoid of interest. The GUI 126 is configured to present various control and results screens to the user 108 and to receive input from the user 108.

FIG. 2C is a block diagram of the instrument assembly 104. The instrument assembly 104 can include various components for imaging the individual cellrafts 130 having the forming or formed organoids loosely attached on the surface and selectively releasing the cellrafts 130 having a forming or formed organoid of interest from the microarray for placement into the collection plate 114. For example, the instrument assembly 104 can include a power breakout board 138 and various control boards for controlling motors and actuators (e.g., PS3 control board 132, PS3 XYZ control board 134, and PS3 FILTER control board 136). The motor control boards can contain TTL and shutter functions that allow the controller 124 to control or address various components of the instrument assembly 104.

The instrument assembly 104 can include a digital camera 140 or other appropriate imaging device, a communications hub (e.g., USB Hub 142), a fluorescence light emitting diode (LED) engine 144, and a light guide adapter 146. The fluorescence LED engine 144 can include multiple narrow-band LEDs configured to illuminate the microarray 112 by way of the light guide adapter 146.

The instrument assembly 104 includes a microscope system (e.g., an internal inverted digital microscope) including a motorized XY stage 148 and an autofocus motor 150 configured for translating a microscope objective 152. Typically, the camera 140 and the fluorescence LED engine 144 and microscope system are arranged in an epi-fluorescence configuration. The microscope system includes a release needle 154 configured for individually releasing cellrafts 130 from the microarray 112. The release needle 154 can be actuated by the autofocus motor 150.

In some examples, the microscope system supports imaging of a region on a microarray having 46×46 cellrafts of 500 micron×500 micron in dimension in a single reservoir, at a resolution of less than 2 microns per pixel in a given field of view. The microscope system may also support the capture of images using brightfield imaging (i.e. white light illumination and white light emission) and the capture of images in one or more fluorescent emission channels. In some examples, the instrument assembly 104 is capable of scanning an entire microarray in under 20 minutes for all three fluorescent channels and brightfield assuming an exposure time 750 ms across all channels.

The release needle 154 typically comprises materials resistant to oxidation when exposed to saline or cell culture media. In some examples, the release needle 154 is a stainless steel 100 micron needle. The release needle 154 can have a possible travel distance of, e.g., at least 15 mm in the X and Y directions with respect to the center of the microarray 112.

The instrument assembly 104 includes a gantry assembly including a belt drive 156 for moving the gantry assembly, a brightfield LED 158 for illuminating the microarray 112 during imaging, and a linear actuator 160 configured for moving a magnetic wand 162 to collect cellrafts carrying a forming or formed organoid after release. The gantry assembly can alternatively use a lead screw instead of a belt drive, or any other appropriate motor. The linear actuator 160 can be, e.g., a stepper motor configured to raise and lower the magnetic wand 162 into and out of the microarray 112 and the collection plate 104.

The instrument assembly 104 includes a collection magnet 164 positioned underneath the collection plate 114 to collect cellrafts into the collection plate 114 from the magnetic wand 162. The collection magnet 164 can have a polarization opposite that of the magnetic wand 162 to repel the magnets within the magnetic wand 162 and pull the cellraft to the bottom of the collection plate 104. The magnetic wand 162 typically comprises a material that is capable of being rendered sterile (e.g., rinsed with ethanol or isopropanol while removed from the instrument) so as not to contaminate the released cellraft or the media used in the collection plate 104. The material for the magnetic wand 162 is also generally selected such that contact with the culture media does not cause any detectable decrement in cell viability or proliferation, or in the performance of molecular biology reagents, such as Taq polymerase, or reverse transcriptase.

Figure 3A:
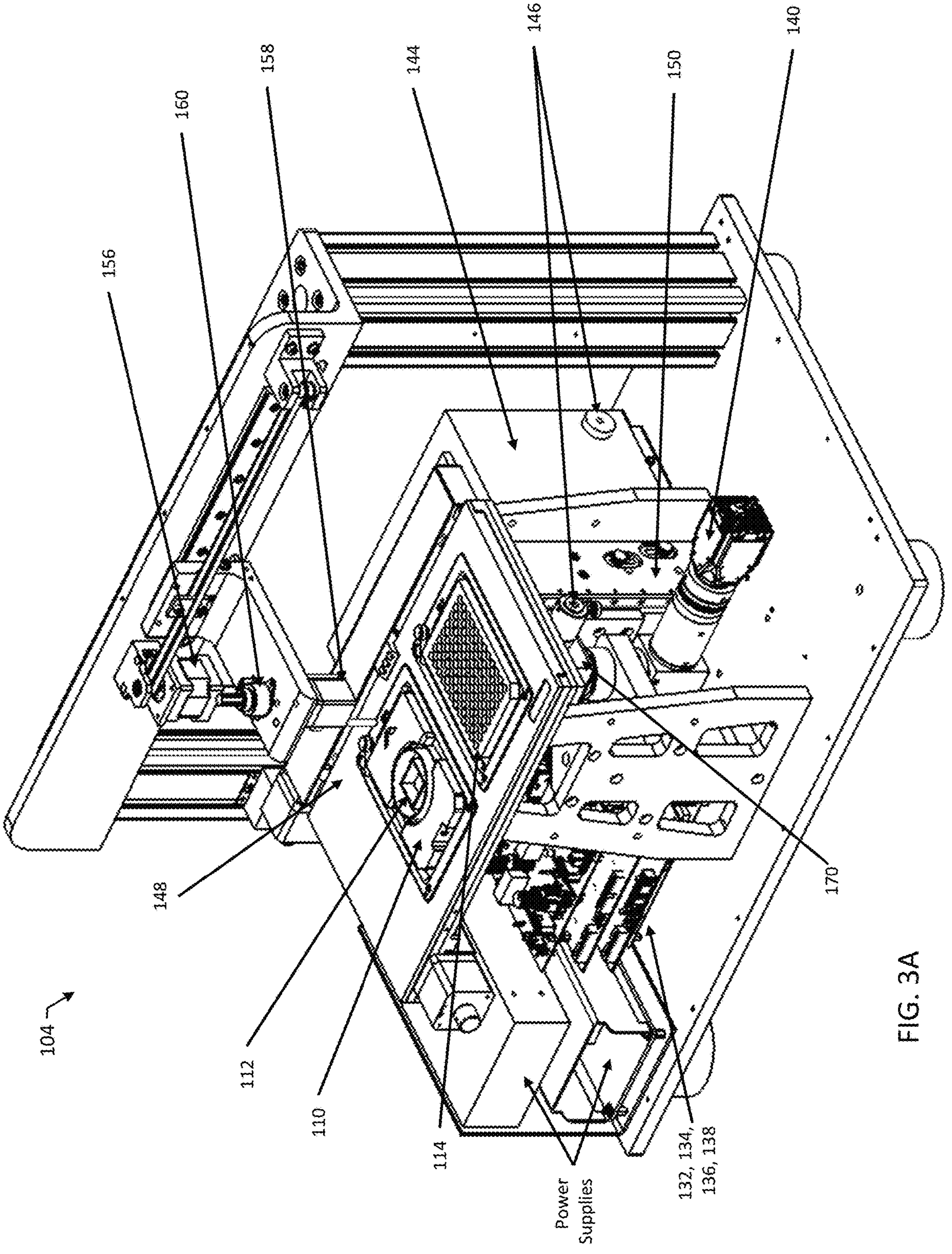
FIG. 3A is an isometric view of an example implementation of the instrument assembly 104 depicted in FIG. 2C for organoid imaging and collection.
Figure 3B:
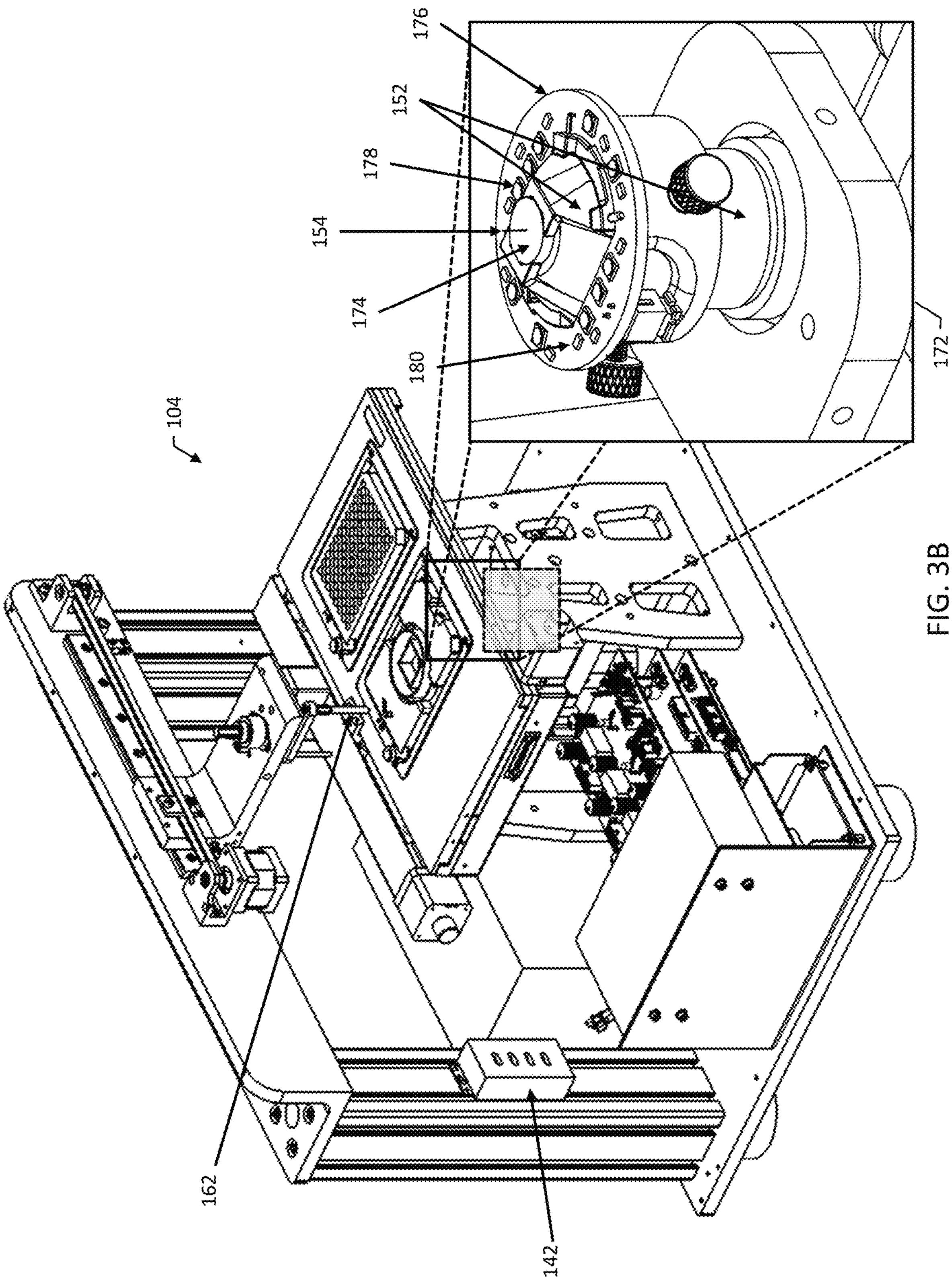
FIG. 3B is an isometric view of an example implementation of the instrument assembly 104 depicted in FIG. 2C for organoid imaging and collection with an inset illustrating a concentric needle design.

FIGS. 3A-3B are isometric views of an example apparatus for organoid imaging and collection. The apparatus is an example implementation of the instrument assembly 104 depicted in FIG. 2C. As shown in FIG. 3A, the adapter plate 110 and the collection plate 114 are positioned on top of the horizontal XY stage 148. Some components, such as the electronic control boards 132, 134, and 136 are located below the XY stage 148. The XY stage 148 is configured to move the microarray 112 and the collection plate 104. The XY stage 148 is electronically controllable for positioning cellrafts for imaging the organoid structures contained on the surface (aligning cellrafts with the microscope objective 152), releasing selected cellrafts carrying the organoid structures of interest (aligning cellrafts with the release needle 154), and depositing the selected cellrafts with organoid cargo (aligning the magnetic wand 162 and selected locations of the collection plate 104 over the collection magnet 164).

The gantry assembly, including the belt drive 156, is positioned vertically over the XY stage 148. The gantry assembly is configured to move laterally to position the brightfield LED 158 for imaging and also to position the magnetic wand 162. The gantry assembly positions the magnetic wand 162 over the microarray 112 to collect cellrafts during release, and then the gantry assembly positions the magnetic wand 162 over the collection plate 114 to deposit cellrafts into selected locations of the collection plate 114.

The camera 140 and the autofocus motor 150 are located beneath the XY stage 148, e.g., so that the autofocus motor 150 can move vertically with respect to the XY stage 148. The fluorescence LED engine 144 and liquid light guide ports 146 are located below the XY stage 148 and coupled to a fluorescence filter cube 170. The fluorescence filter cube 170 is configured for fluorescence imaging, e.g., to allow light from the fluorescence LED engine 144 to reach the microarray 112 and to block that light from reaching the camera 140.

FIG. 3B shows a cut-away view 172 of the microscope objective 152 and the release needle 154. As shown, the release needle 154 is located within the field of view of the microscope objective 152. Locating the release needle 154 in the field of view of the microscope objective 152 enables visualization of the release of a cellraft with organoid cargo in real time, which is required to accurately position the release needle for dislodgement of the larger cellraft carrying an organoid structure embedded in ECM from the elastomeric substrate of the microwell. However, this location of the release needle in alignment with the microscope optical axis can require imaging through a window 174 of material, such as acrylic, that is transparent and can be machined to mount the release needle 154. This can reduce the transmission of the excitation and emission light and require longer integration times during scanning. In addition, the magnetic wand 162 is positioned above the target cellraft during release to affect more rapid collection of the cellrafts; however, in this geometry, the lateral position of the brightfield LED 158 is offset from the microscope objective 152 and the magnetic wand 162 casts a shadow of its light. To solve these issues, the assembly comprising the release needle 154 as illustrated in FIG. 3B can include an annular printed circuit board 176 containing light-emitting diodes 178 and resistors 180 to provide epi-illumination of the microarray and cellraft targeted for release. The light from the diodes 178 travels upward through the microarray 112 and is reflected by the tip of the magnetic wand 162—positioned inside the fluid within the reservoir of the microarray 112—to create pseudo-transillumination of the cellraft as it is released.

It can be useful to calibrate the offset between the center of the field of view of the microscope objective 152 and the puncture location of the release needle 154 on the microarray 112. Calibration can be performed, e.g., after every needle replacement, or at the start of every experiment, or one time during manufacturing. In some examples, the controller 124 of FIG. 2B is programmed to perform automated calibration.

For example, the controller 124 can move the microarray 112 to position the field of view of the microscope objective 152 with a microarray border, autofocus the microscope objective, and then puncture the microarray border with the release needle 154. Then, the controller 124 acquires an image (e.g., using the brightfield LED 158) and analyzes the image to locate the puncture position, e.g., by segmenting the image. The controller 124 can then calculate an offset. In some examples, the controller 124 repeats the process a specified number of times by moving to different locations and determines a calibration distance based on the offset positions, e.g., by averaging the offset positions. In some other examples, the controller 124 can move a microarray 112 that does not contain cellrafts to position the field of view of the microscope objective 152 with a microwell in the center of the microarray 112, autofocus the microscope objective, and then puncture the microarray with the release needle 154. Then, the controller 124 acquires an image (e.g., using the brightfield LED 158) and analyzes the image to locate the puncture position, e.g. by segmenting the image, or prompts the user to locate the puncture position, e.g. by clicking on a display of the image. The controller 124 can then calculate an offset. In some examples, the controller 124 repeats the process a specified number of times by moving to different microwells and determines a calibration distance based on the offset positions, e.g., by averaging the offset positions.

To test the image quality of brightfield and widefield fluorescence z-stacks acquired by the automated system, two 200-300 μm mouse hepatic organoids were selected on a microarray stained with Hoechst and EpCAM (primary antibody conjugated with FITC) for imaging (as described in Example 2). Brightfield, blue fluorescence (exposure=50, 50 ms), and green fluorescence (exposure=200, 100 ms) images were acquired every 10 μm across focal ranges that encompassed the full height of the two organoids (24 and 30 images, respectively). The brightfield and false-colored fluorescence images (FIG. 4A) demonstrate excellent image quality with the ability to visualize individual cells, cell junctions (green), and substructures within nuclei (blue), including mitotic figures.

To leverage the phenotypic content in the z-stack images, 1) an intuitive user interface within the software is provided for users to visually explore each image stack through composite brightfield and fluorescence display (FIG. 4B); and 2) automated algorithms are provided to measure organoid diameter and other morphologic and phenotypic parameters to identify and group organoids based on size or other metrics, whether for phenotypic assessment or isolation thresholds. This includes assessment of large organoids (>500 μm) that overgrow the cellraft footprint and require image processing into neighboring cellrafts. Z-stack images can be additionally exported for display and manipulation using external software. This combination of expanded software capability allows for automated phenotypic characterization of individual organoids that is not possible using standard organoid culture methods and imaging platforms, with the option to designate any organoid-containing cellraft of interest for isolation from multiple screens within the software.

Figure 5A:
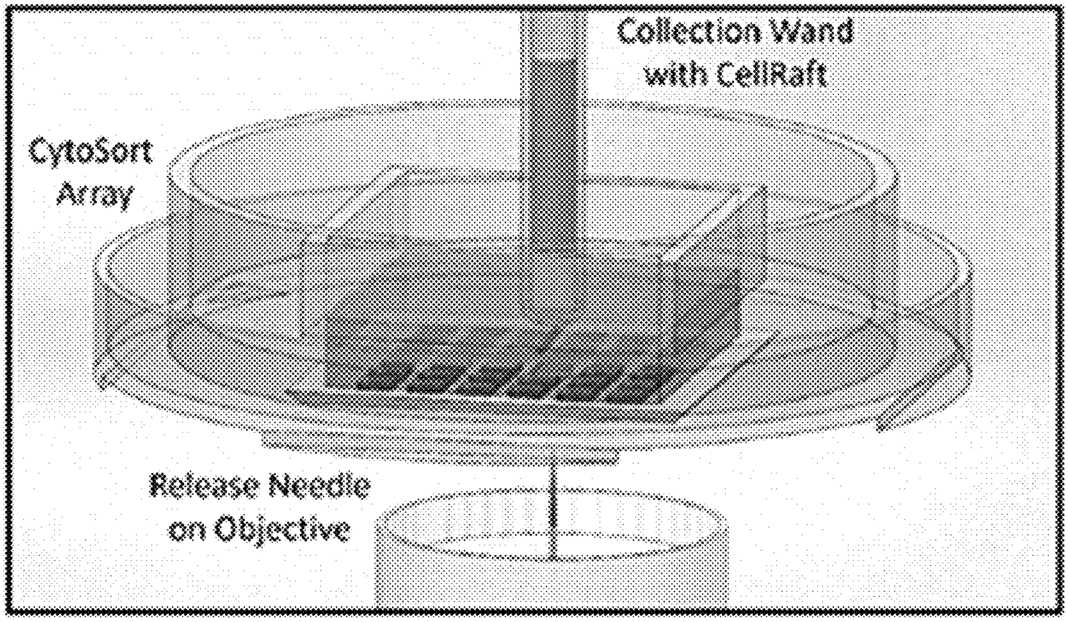
FIG. 5A is a schematic of the system of the present disclosure that enables automated isolation and transfer of organoid-containing cellrafts from the microarray, where first, the release needle punctures the elastomeric floor of the microarray to dislodge the cellraft from its microwell, and next the collection wand, which houses a retractable magnet, is lowered into the microarray to collect the released cellraft, which is doped with paramagnetic iron nanoparticles.
Figure 5B:
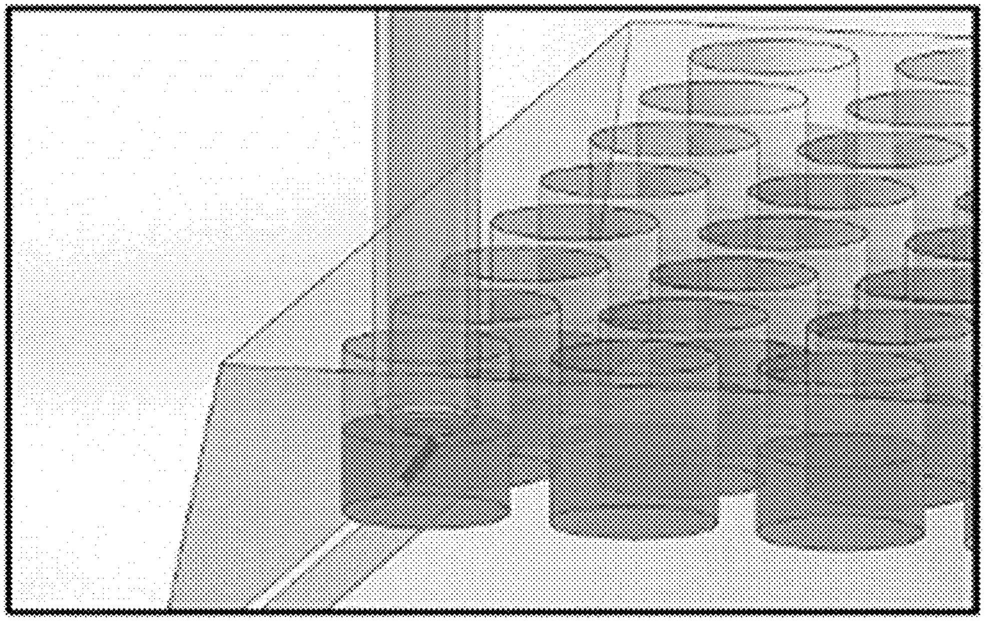
FIG. 5B is an illustration a zoomed in portion of FIG. 3A, where the collection wand is inserted into the designated well of a 96-well plate or PCR tube while the internal magnet is retracted, allowing the cellraft to fall into the well.

Embodiments of the automated system of the invention provide image-driven cellraft isolation. In one example, after performing automated imaging using the system, the user can identify forming or formed organoids of interest and designate cellrafts for isolation using a variety of software-guided or manual selection tools. Once selected, a cellraft is dislodged from its microwell by a motorized release needle that penetrates the elastomeric bed of the microarray (FIG. 5A) and, because of paramagnetism in the exemplary case of a cellraft doped with iron nanoparticles, collected on the tip of a magnetic wand. The system then aligns and inserts the wand into the designated well of a 96-well tissue culture or PCR plate, while retracting its internal magnet, to deposit the cellraft carrying the forming or formed organoid in the collection plate (FIG. 5B). The process is repeated for each cellraft selected by the user for isolation, one cellraft (with its attached organoid structure) per collection well.

Figure 5C:
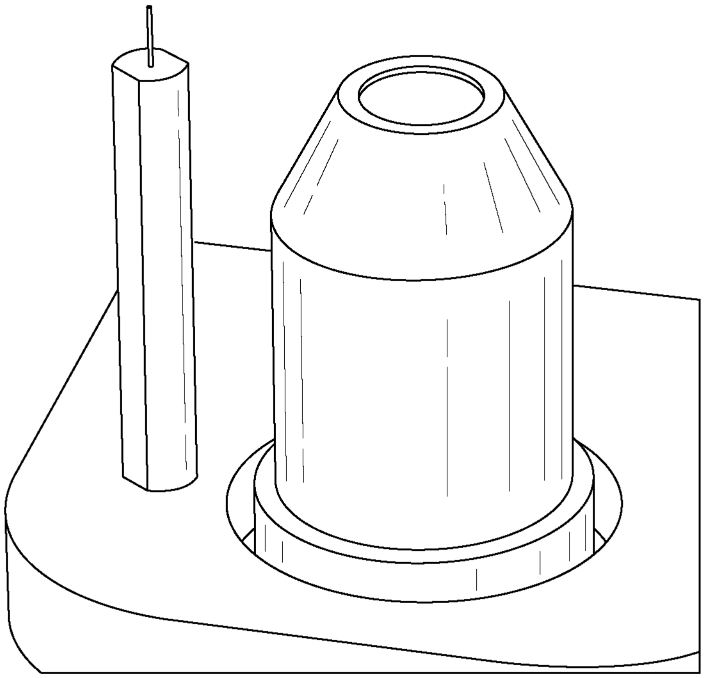
FIG. 5C is an illustration showing the original "off axis" needle of a previous design which relies on factory calibration to conduct prescribed "pokes" for cellraft release.

With the previous CellRaft AIR System, the process has been validated (>95% success rate) to release 100 μm and 200 μm cellrafts in liquid culture media from their microwells using a regimented 2-poke pattern and then to collect them with the magnetic wand positioned up to 5 mm away. With the previous CellRaft AIR System, the prescribed poke locations and large attraction distance have allowed cellraft isolations to be conducted “off axis” from the microscope imaging path (FIG. 5C), relying on system calibration between the microscope, needle, and wand to align the cellraft of interest for release and collection.

Figure 5D:
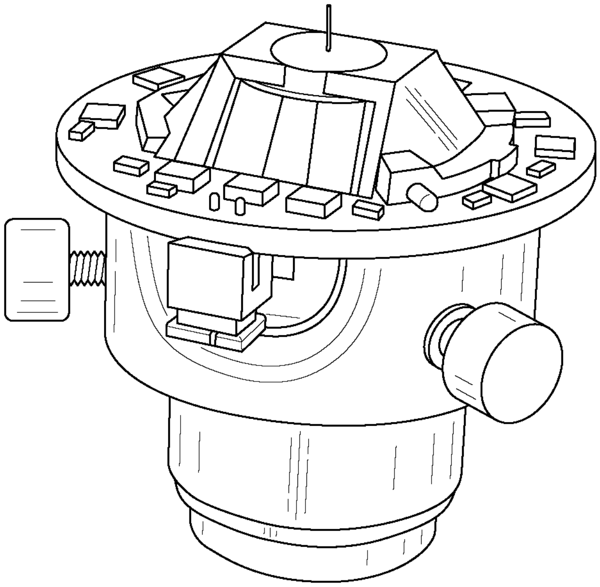
FIG. 5D is an illustration showing the design of the automated system of the present disclosure where the concentric needle design aligns the release needle with the objective, enabling dynamic image-based guidance of the release needle (and magnetic wand), which increases the accuracy and speed of dislodging (and collecting) organoid-containing cellrafts in extracellular matrix.
Figure 5E:
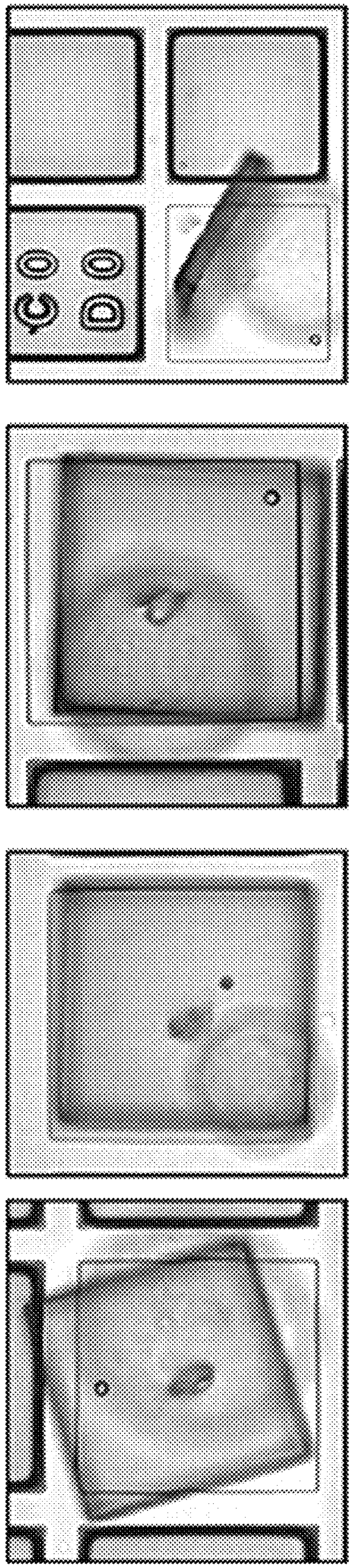
FIG. 5E is a series of images showing release of a cellraft using the automated system of the present disclosure.

Release of cellrafts larger than about 400 μm, e.g., 500 μm cellrafts, from the microarray and collection through an extracellular matrix are significantly more challenging than in liquid cell culture. Release from the microarray requires a more targeted needle poke to release cellraft corners that remain engaged with the elastomeric microwell and much closer proximity (0-1 mm) of the magnetic wand tip to the cellraft to overcome the ECM viscosity. To address these challenges, a “concentric” release needle design (FIG. 5D) was developed and validated to align the release needle and collection wand with the microscope imaging axis, which facilitates real-time imaging of cellraft release and three-dimensional alignment of the collection wand tip to the target cellraft. Imaging data is instantly analyzed to achieve and detect cellraft release (FIG. 5E) after 1-4 targeted needle pokes and to dynamically control the height, lateral position, and dwell time of the magnetic wand tip to achieve cellraft collection. The concentric design of the system hardware, paired with the system software that performs image-based decisions, yields faster organoid isolation with a higher success rate than the previous “off axis” CellRaft AIR System.

Figure 6A:
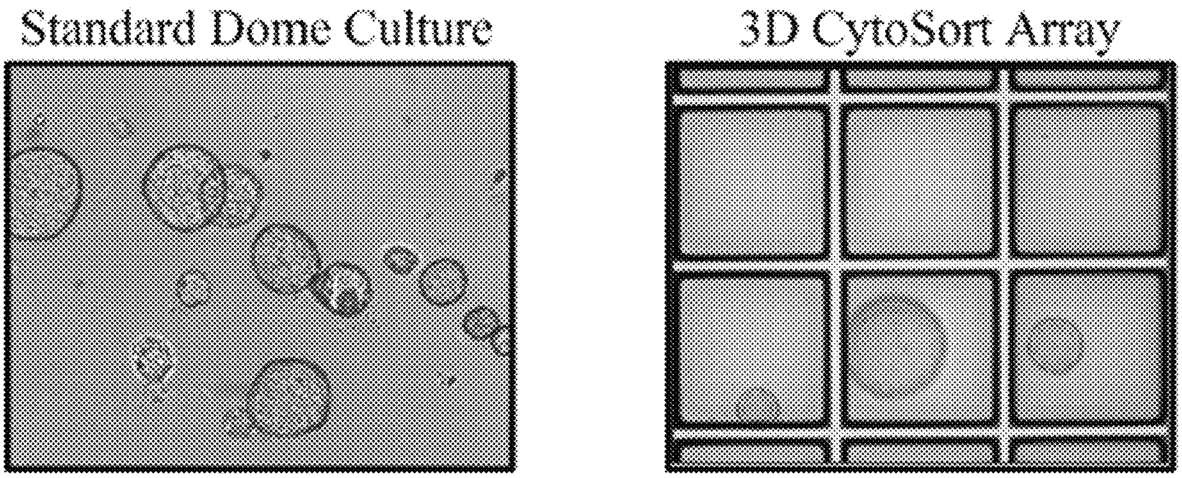
FIG. 6A illustrates an image on the left showing a traditional dome culture method for organoids that presents challenges in imaging and clonal propagation due to random arrangement of organoids in the x, y, and z dimensions in contrast to an image on the right showing organoids cultured according to the methods of the present disclosure where the organoids are organized in segregated microwells in a single focal plane on the microarray.

In some embodiments of the invention, a number of organoid workflows are enabled by the microarray and automated system including clonal identification and temporal phenotypic assessment of organoids on the microarray. Traditional culture methods of organoids in semi-solid basement membrane extract (BME) dome, such as Matrigel, result in random arrangement in the x, y, and z dimensions, making imaging challenging due to overlapping 3D structures and multifocal imaging requirements. In addition, the random arrangement of cells in a BME dome docs not permit clonal organoid growth or temporal growth assessment of individual organoids (FIG. 6A). The larger microarray of the invention, e.g., the exemplary 500×500 μm microarray, which provides segregated microwell positions that have unique IDs, and a revised seeding protocol (see Example 2), which facilitates alignment of organoids onto the predictable z-plane of the microwells, overcome this bottleneck of traditional organoid culture methods. The system in combination with the exemplary 46×46 cellraft microarray provides an automated solution to temporally image more than 2,100 available cellraft, or organoid, positions on a single cell culture consumable. In one embodiment, images captured for each cellraft are automatically stored in system software providing a complete, easily viewable data record for each organoid.

Figure 6B:
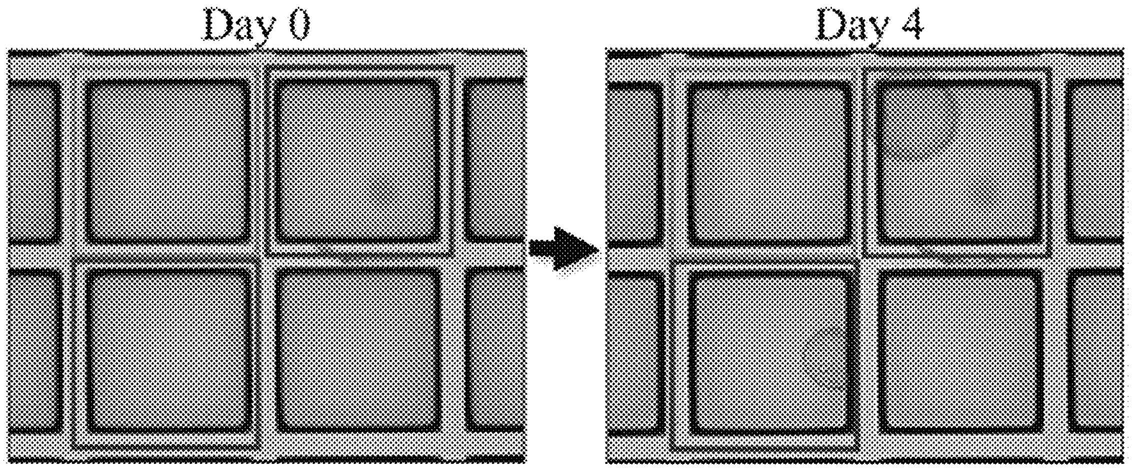
FIG. 6B illustrates that organoids cultured using the methods, microarray, and automated system of the present disclosure enable clonal propagation and temporal monitoring of clonal organoid development, with serial imaging, beginning 4 hours after cell seeding (Day 0) on the microarray, cellrafts with single cells (green box), or small clusters of cells (red boxes), can be easily identified using the system software and tracked over time.
Figure 6C:
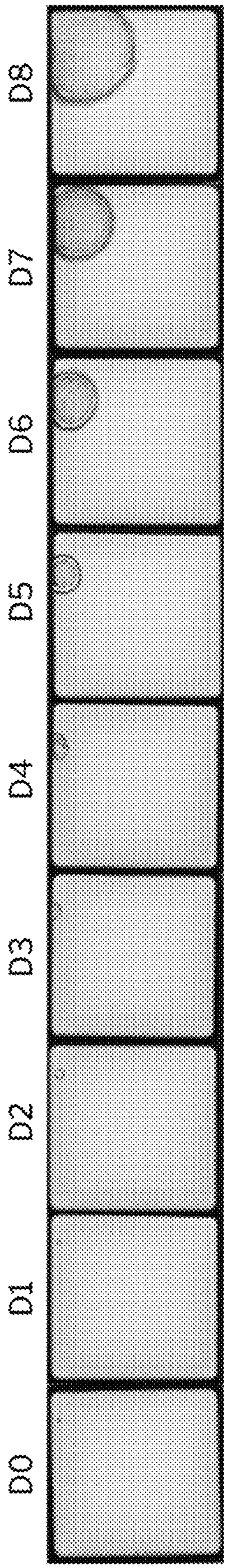
FIG. 6C is a series of images of the microwells of the microarray taken over 8 days illustrating that the system and methods of the present disclosure allows for a complete data record that verifies clonality.
Figure 7:
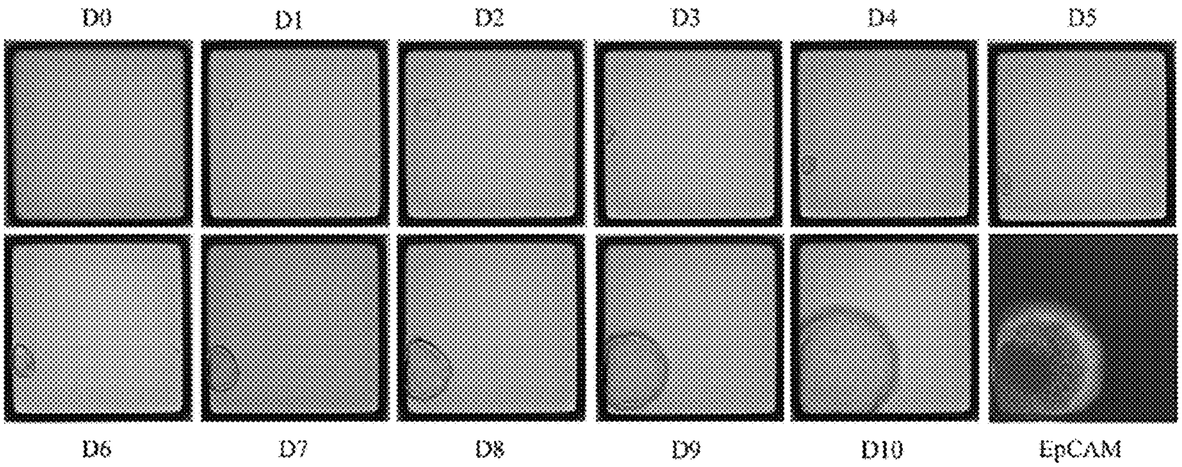
FIG. 7 is a schematic showing temporal imaging of the development of a mouse hepatic organoid from a small fragment of cells for 10 days on the microarray, where on day 10, the organoids on the microarray were stained with a FITC-conjugated primary antibody for EpCAM and imaged for phenotypic assessment.
Figure 12A:
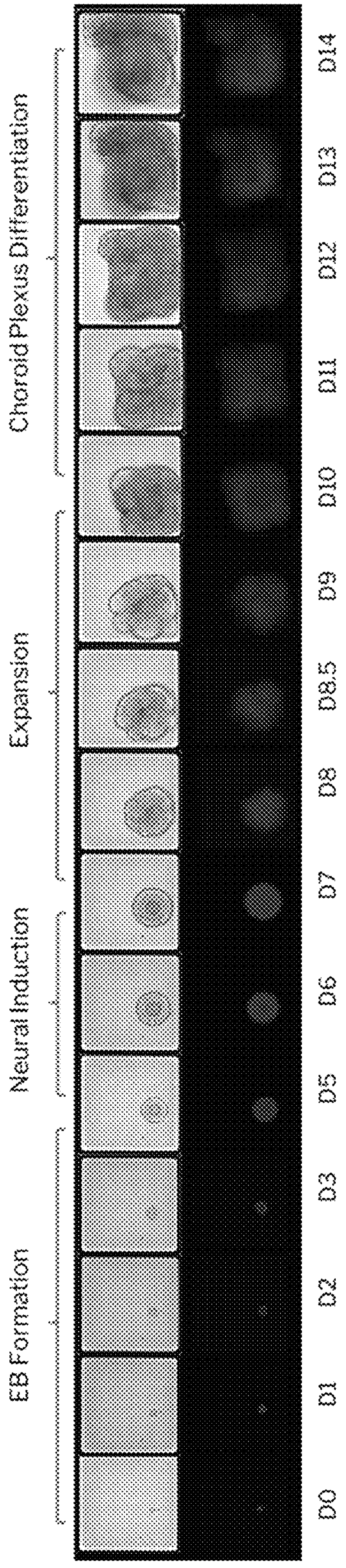
FIG. 12A is a series of images of the microwells of the microarray taken over 14 days illustrating differentiation of RFP+ iPSCs into choroid plexus organoids demonstrating that the system and methods of the present disclosure allows for a complete data record and phenotypic monitoring of differentiation from pluripotent stem cells to 3D organoids.
Figure 12B:
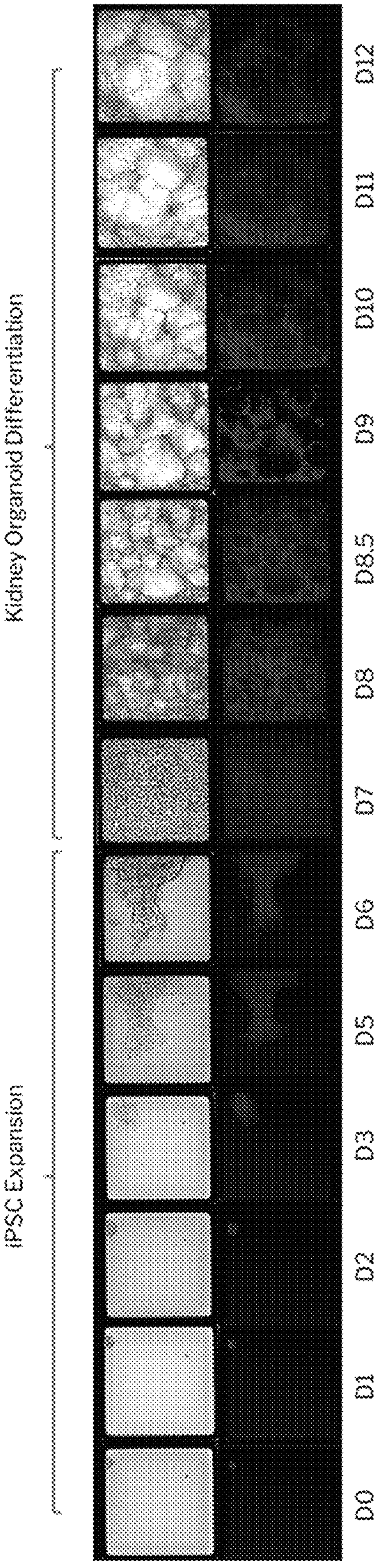
FIG. 12B is a series of images of the microwells of the microarray taken over 12 days illustrating differentiation of RFP+ iPSCs into kidney organoids demonstrating that the system and methods of the present disclosure allows for a complete data record and phenotypic monitoring of differentiation from pluripotent stem cells to 3D organoids.

Using both mouse pancreatic (FIG. 4C) and mouse hepatic organoids, a robust and reliable method is demonstrated for obtaining high-quality, time-course images of developing organoids on the microarray (see Example 3). In addition, the methods described demonstrate the ability to monitor differentiation of pluripotent stem cells into organoids (FIGS. 12 and 13) of a variety of tissue types, including kidney, choroid plexus, cerebral (see Example 5). A dynamic growth record of each organoid can be maintained during the entire development process from single cell to isolation. In one example, beginning with an array scan shortly after cell seeding (i.e., loading of an organoid fragment or single cell suspension onto the microarray) (4 hours), the user can identify cellrafts with single or multiple cells either manually or by using a CellRaft Cytometry tool (Cell Microsystems, Inc., Durham, NC) (FIG. 6B). The ability to reliably image the forming or formed organoid on each cellraft in every field of view on the microarray can enable clonal organoid workflows that are not currently possible using standard culture methods and imaging tools. Subsequent serial scans of the microarray can then be initiated by the user at desired time intervals to capture temporal images of organoid development (FIG. 6C, FIG. 7). The system can acquire a full array scan in brightfield and three fluorescent channels in under 15 minutes (under 9 minutes for brightfield only), providing a rapid solution for multiparameter phenotypic and morphologic screening of hundreds of individual organoids.

Figure 4A:
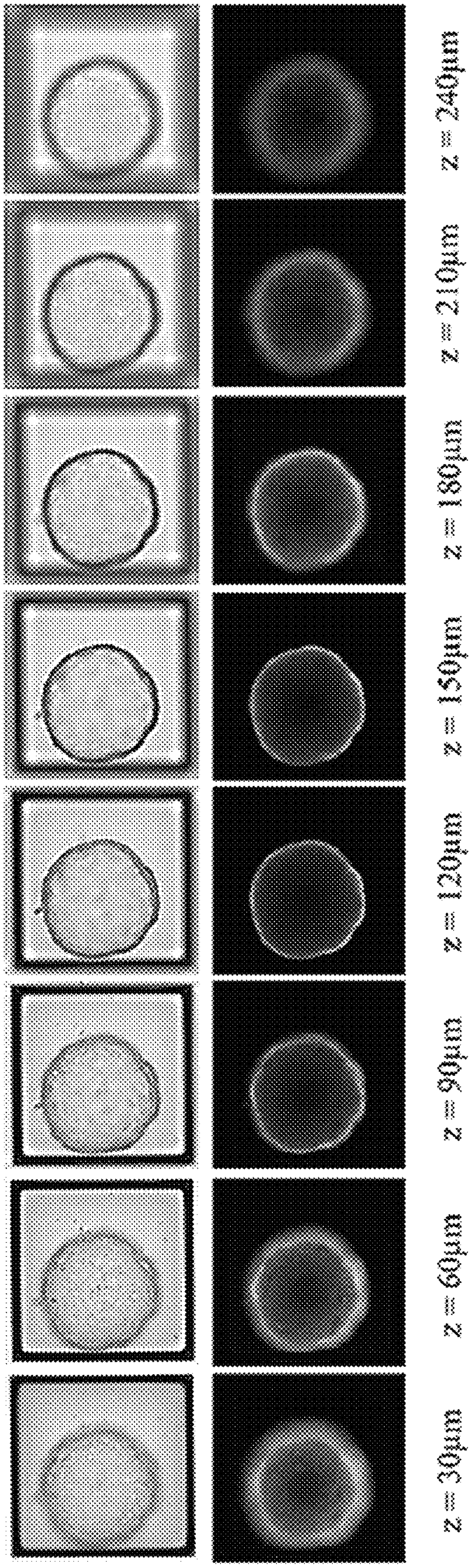
FIG. 4A is a series of images acquired using the automated system, where the software includes automated z-stack acquisition in brightfield and 3-color fluorescence for organoids of interest. Mouse hepatic organoids were co-stained with a FITC-conjugated antibody for EpCAM and Hoechst 33342 to highlight cell membranes (green) and nuclei (blue). Using the automated system, z-stack images were taken every 10 μm through the full height of the organoid.
Figure 4B:
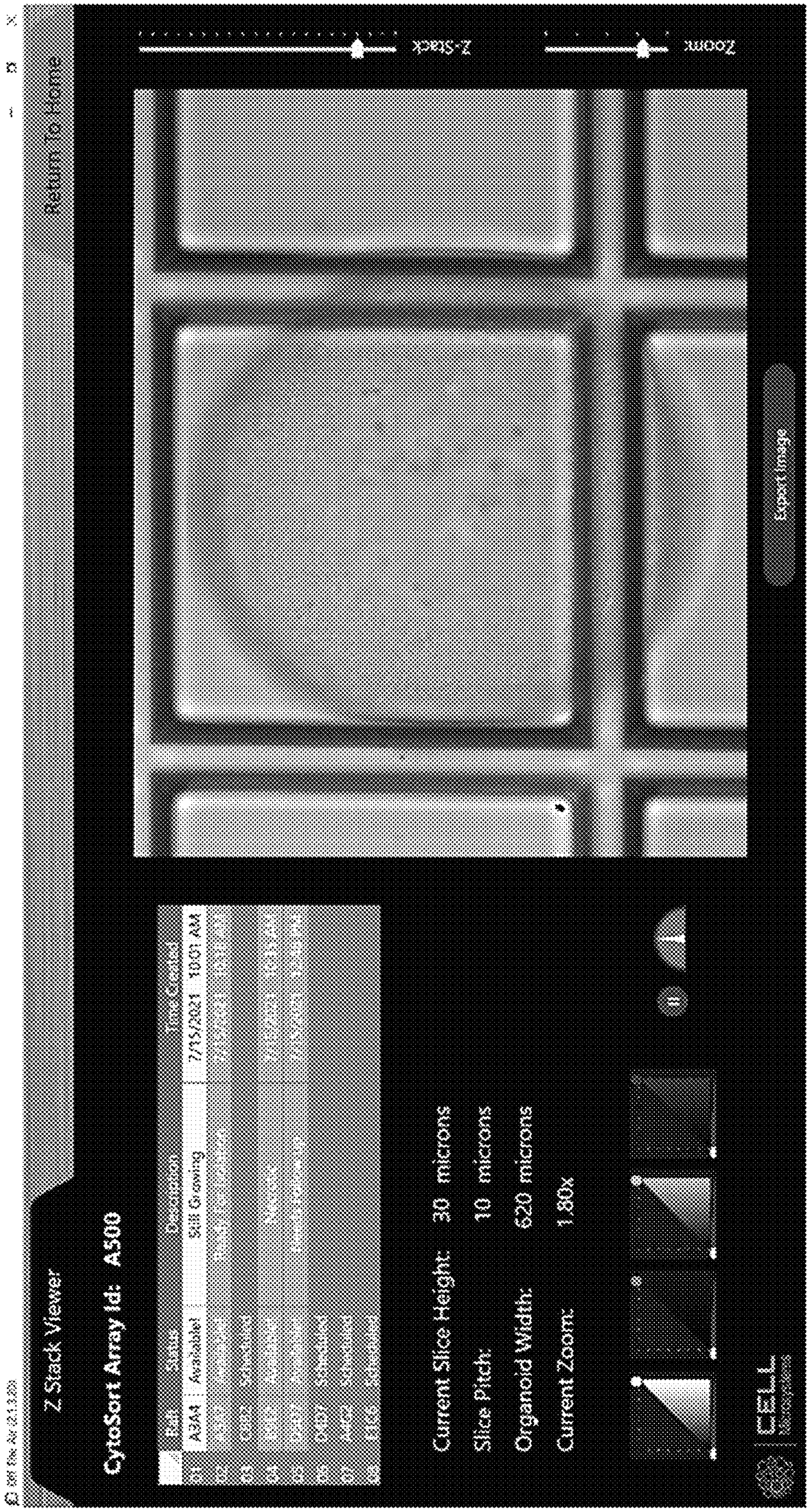
FIG. 4B is an image showing one example of the system software of the invention, and companion OFF THE AIR data analysis software, which provides a user-friendly, intuitive interface to automatically acquire and explore z-stack images of organoids of interest. After the user defines the z-stack slice pitch and brightfield and fluorescence exposures, the software acquires the images across the full organoid height. After image acquisition, the user can easily view each image that was captured within the stack. The software reports the organoid diameter (width), allows the user to zoom in and out of each image to visualize the organoid at single-cell resolution, and provides tools to modify the relative contrast of each imaging channel for composite display. The software also allows the user an area to write in a "description" of each organoid of interest that was imaged, providing a complete data catalog of individual organoids.
Figure 4C:
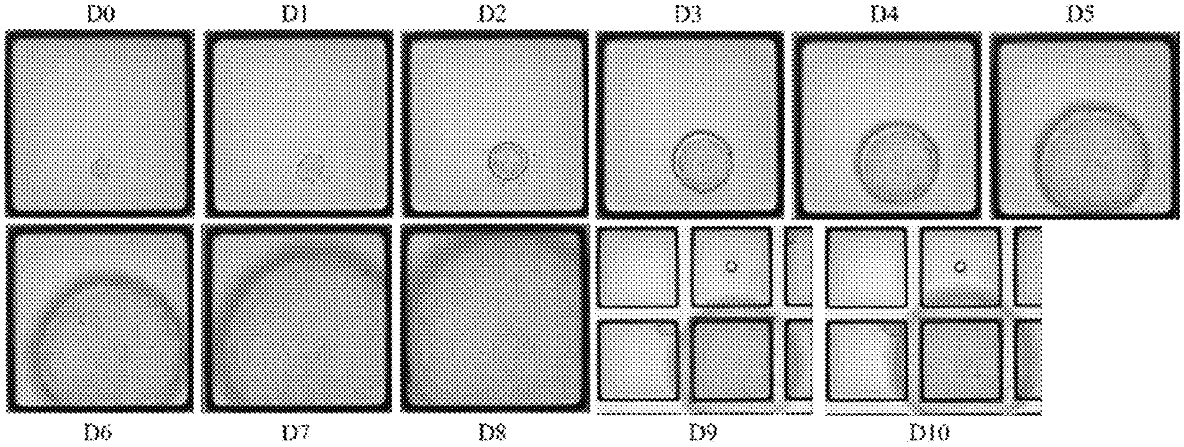
FIG. 4C is a series of images showing temporal imaging of mouse pancreatic organoids on the microarray. Mouse pancreatic organoids were mechanically dissociated into small fragments and seeded on the microarray in dilute Matrigel media. Serial scans of the array were performed every 24 hours for 10 days to monitor organoid development.
Figure 5F:
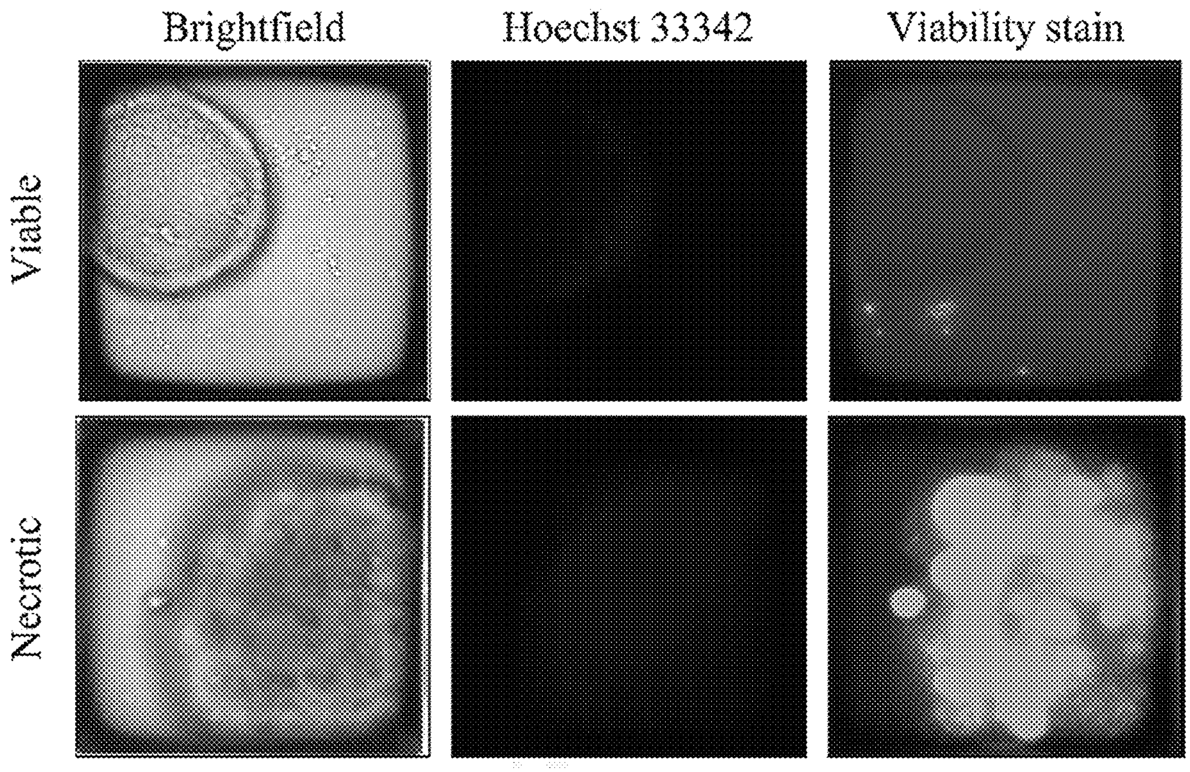
FIG. 5F is a series of images using the brightfield and fluorescence imaging capabilities of the system, where mouse pancreatic organoids were assessed for viability using the ReadyProbes Blue/Green Cell Viability kit (Invitrogen). Individual organoids are easily imaged and assessed for viability, including necrotic cores.

In addition to brightfield imaging, the system can perform advanced fluorescence-based phenotypic assessment for a variety of applications, including, but not limited to, live cell staining, CRISPR editing, and on-array viability assays (FIG. 5F). For example, mouse hepatic organoids stained with FITC-conjugated antibody for EpCAM demonstrate detailed visualization of cell membranes (FIG. 4A, FIG. 7) and Hoechst-stained nuclei enable cell counting throughout the z-stack (FIG. 4A). Such temporal brightfield and fluorescence imaging that can be applied to hundreds of individual organoids on a single microarray using the system represents a significant advancement over current methods that require dozens of standard cell culture consumables, expensive imaging platforms, and extensive manual upstream and downstream effort by the user.

In various embodiments, organoids are isolated from the microarray for downstream assays, growth and subcloning, and -omics applications. In addition to the issue of multi-focal imaging requirements, traditional organoid culture methods are susceptible to producing large variations in organoid size, shape, viability, and growth rate due to inconsistent starting material. Standard Matrigel dome culture methods used to evaluate organoid development, viability, or molecular-based changes in response to toxicants or therapies homogenize the response of many organoids, ignoring phenotypic and genetic heterogeneity. With the microarray and system of the invention, a solution is provided for investigating heterogenous organoid populations, as well as generating clonally derived organoid populations. In addition to image-based phenotypic characterization, the microarray and system permit isolation and transfer of individual organoids of interest for downstream applications and expansion.

Figure 8A:
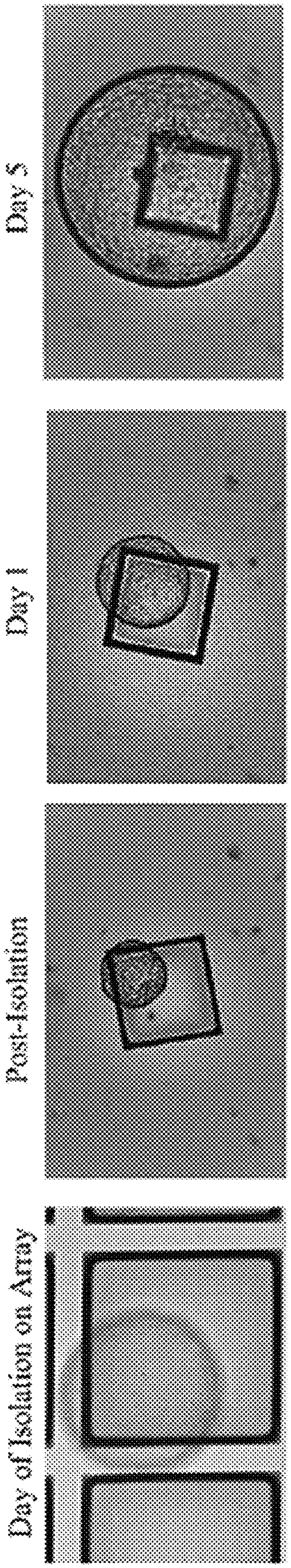
FIG. 8A is a schematic of images showing that organoids isolated from the microarray and system of the present disclosure continue to grow post-isolation and can be used for downstream applications, including organoid sub-cloning.

Using organoid models to understand the dynamics and evolution of intra- and inter-tumor heterogeneity on the molecular level is becoming widely used to better predict drug efficacy. While studies have been performed using standard culture methods, largely focused on populations of organoids, the reliability and efficiency of the disclosed system for enabling such applications for individual organoids is demonstrated. For example, the utility of the disclosed system for downstream organoid growth and subcloning, and nucleic acid isolation from individual organoids isolated from the microarray is demonstrated using both mouse pancreatic (data not shown) and mouse hepatic organoids (see Example 4). Specifically, after isolation from the microarray into 96-well collection plates, organoids remain viable for downstream assays and continue to grow in dilute Matrigel growth media (FIG. 8A).

Figure 8B:
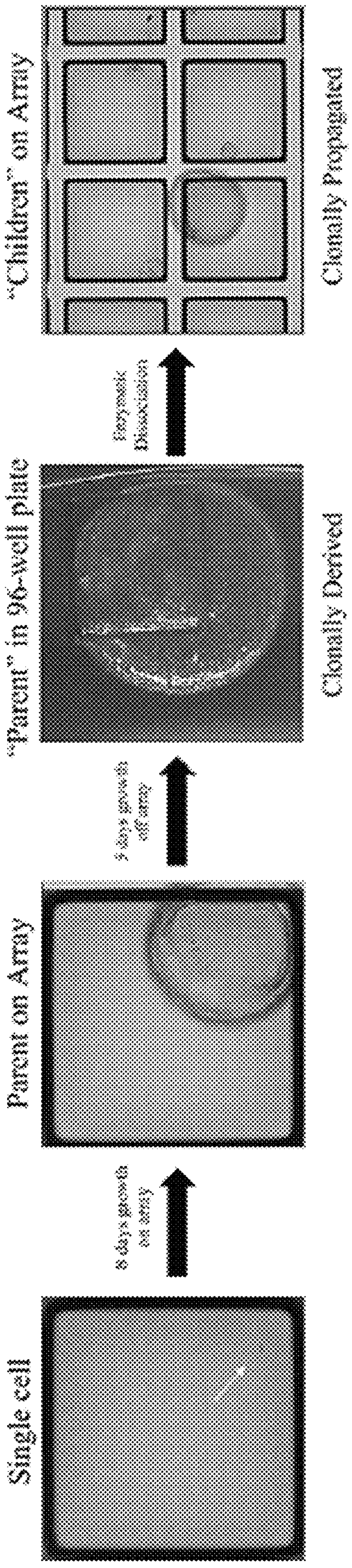
FIG. 8B is a schematic of images showing mouse hepatic organoids that were isolated as in FIG. 6, 8A and subsequently dissociated into single cells and seeded onto a second microarray and imaged every 24 hours for 8 days to monitor clonal organoid development. Specifically, clonal "parent" organoids were isolated into 96-well collection plates, containing dilute Matrigel media, using the automated system and allowed to grow for 5 additional days off-array. In the 96-well collection plate, individual "parent" organoids were enzymatically dissociated, and the second-generation "child" cells were seeded onto a second microarray for clonal organoid propagation.

The ability to create clonal organoid populations by leveraging the imaging and isolation capabilities of the disclosed system is also demonstrated (see Example 4). For example, organoids derived from single cells are identified as verified by temporal imaging on the microarray and the identified organoids can be isolated into 96-well collection plates using the automated system. After 5 days of growth off-array, each "parent" organoid can be enzymatically dissociated in the 96-well plate into small fragments of cells, then re-seeded onto a new microarray to propagate hundreds of second-generation "child" organoids for further expansion or evaluation of lineage-based phenotypes (FIG. 8B).

Figure 9:
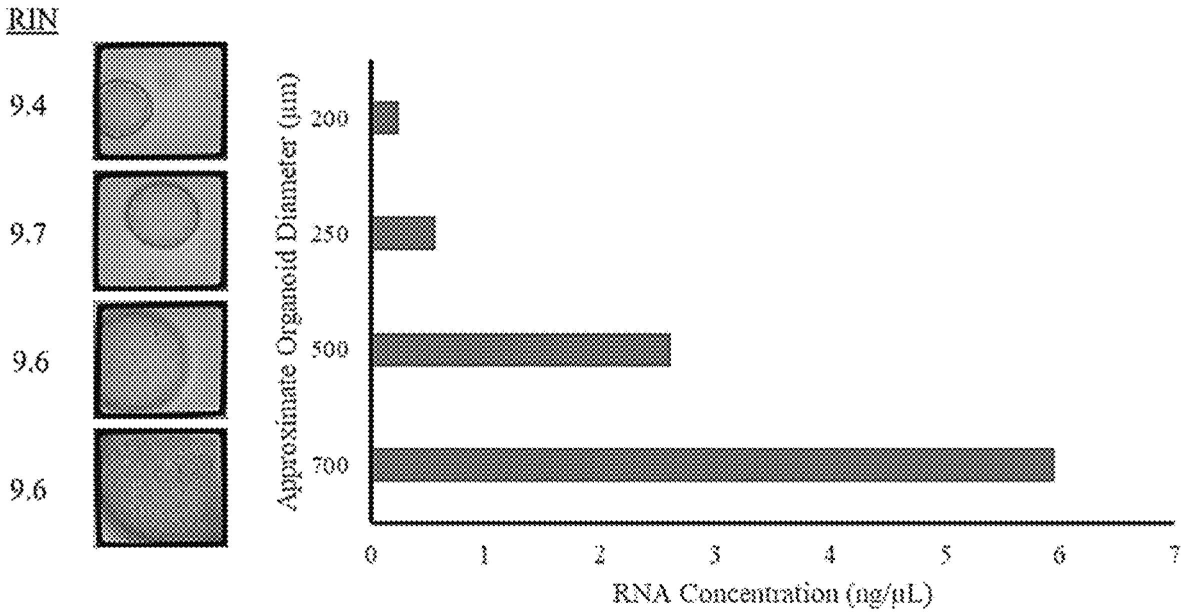
FIG. 9 is a schematic showing that by using the system of the present disclosure, single organoids can be isolated from the microarray for downstream-omics applications. Mouse hepatic organoids, grown to various sizes (200-700 μm) on the microarray, were isolated into PCR strip tubes containing lysis buffer for RNA isolation. High quality RNA was purified from all organoids (RIN>9.4) and RNA concentration was correlated to organoid diameter.

In addition to performing single organoid isolations for downstream growth, assays, and subcloning, the system can deposit single organoids into PCR strip tubes or 96-well PCR plates for nucleic acid isolation, a commonly investigated endpoint for drug discovery and toxicology. In one example, mouse pancreatic (data not shown) and mouse hepatic organoids are seeded onto microarrays and temporal scans are performed to monitor organoid development (see Example 4). Organoids ranging in size, greater than 1 mm, can be isolated directly into a collection plate such as, but not limited to, standard PCR strip tubes. In one embodiment, the organoids range in size from 200 to 700 μm. In one embodiment, organoids of a desired size range are isolated directly into lysis buffer in standard PCR strip tubes for RNA purification. In one embodiment, a size threshold for RNA quality and concentration is determined. High-quality RNA (RIN>9.4) suitable for use in downstream-omics applications can be obtained. The amount of RNA obtained can be directly correlated with organoid size (FIG. 9). The data presented demonstrate the flexibility and utility of the automated system including the microarray to provide an all-in-one platform that facilitates efficient, user-friendly workflows for temporal phenotypic assessment of individual organoids upstream of single organoid applications.

Figure 10:
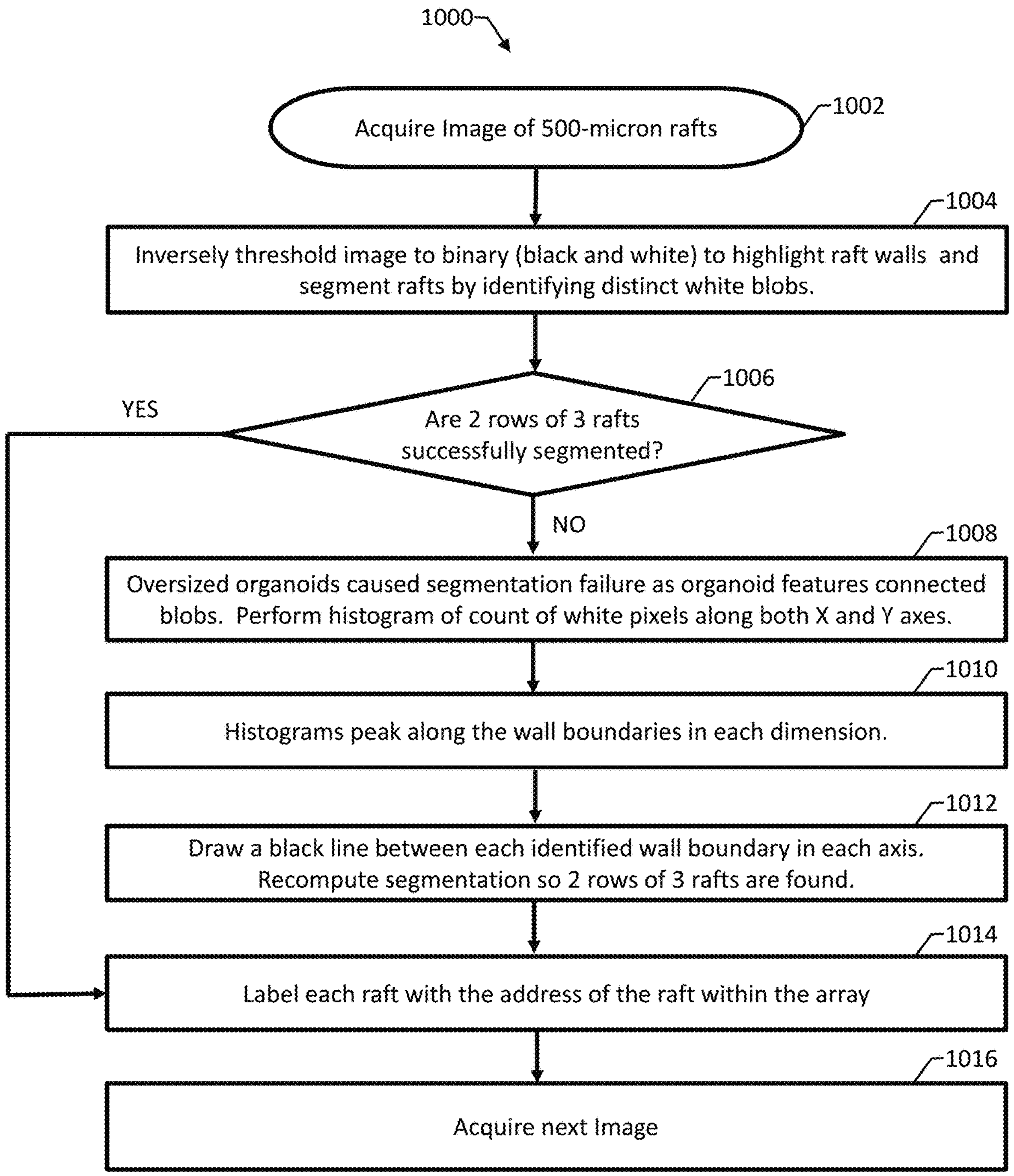
FIG. 10 is a flow chart of an example method for processing images of cell rafts depicting organoids.

FIG. 10 is a flow chart of an example method 1000 for processing images of cell rafts depicting organoids. The method 1000 can be performed by a computer system, e.g., the computer system 102 of FIG. 2A.

Figure 11A:
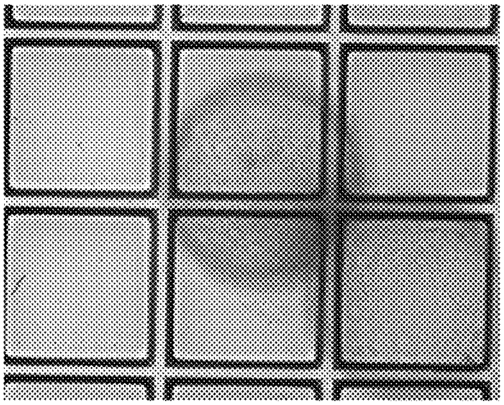
FIG. 11A is an example image of cell rafts depicting an organoid.

The method 1000 includes acquiring an image of cell rafts, e.g., 500-micron rafts (1002). FIG. 11A shows an example of an image of cell rafts.

The method 1000 includes inversely thresholding the image to binary (black and white) to highlight raft walls and segmenting rafts by identifying distinct white blobs (1004). The method 1000 includes determining whether 2 rows of 3 rafts have been successfully segmented (1006). If segmentation was successful (YES), then the method 1000 includes labelling each raft with the addresses of the raft within the array (1014) and then moving on to the next image (1016).

Figure 11B:
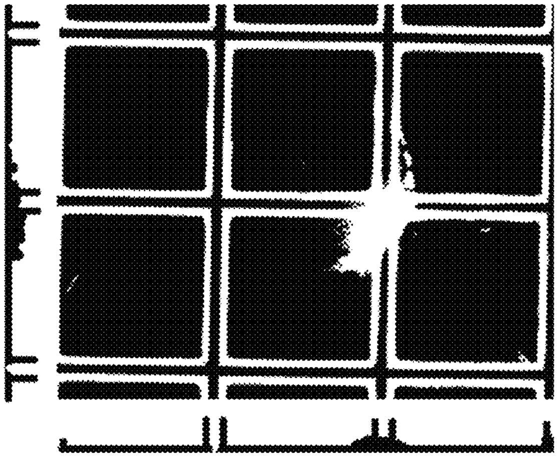
FIG. 11B shows the example image with histograms drawn alongside each of the X and Y axes.

If segmentation was not successful (NO), then oversized organoids caused segmentation failure due to organoid features creating connected blobs. The method 1000 includes performing a histogram of a count of white pixels along both X and Y axes (1008). The resulting histograms peak along the wall boundaries in each dimensions (1010). FIG. 11B shows the example image from FIG. 11A with histograms drawn alongside each of the X and Y axes.

Figure 11C:
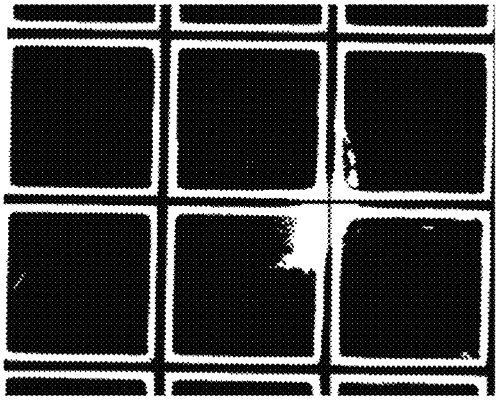
FIG. 11C shows the example image with lines drawn between wall boundaries.

The method 1000 includes drawing a black line between each identified wall boundary in each axis (1012). FIG. 11C shows the example image from FIG. 11B with black lines drawn between identified wall boundaries. Segmentation is recomputed so that 2 rows of 3 rafts are found. Then, the method 1000 proceeds after successful segmentation, i.e., by labelling each raft with the addresses of the raft within the array (1014) and then moving on to the next image (1016).

FIGS. 16A-16C, 17, 18, and 19A-19D illustrate an example system that provides users the ability to query analysis data retrieved during scanning on the system 100. The feature names provided in the examples are shown for purposes of illustration.

In general, the system includes software configured for analyzing data collected by the system 100 and a user interface for receiving queries and presenting results. These queries can be structured to run analysis on cell morphology and across time if multiple scans of a single CytoSort array is taken on the system 100. Analysis on cell morphology is achieved using a feature called "Populations." Analysis across time is achieved using a function called "Venn Diagram."

The system can include a function, which can be called "Single Populations," that is configured for finding cells in the CytoSort array that match a set of criteria based on the features extracted during image processing. A single Population will only focus on a single scan, meaning it focuses only on a single point in time. This means that the focus of a Population is to identify cellrafts that contain specific objects at a single timepoint.

One example could be a Population that retrieves all the cellrafts containing single cells on the first scan taken using the system 100. A second example would be a Population that focuses on identifying all cellrafts that contain a colony of cells on the second scan of a CytoSort Array taken by the system 100.

Each Population has a set of search criteria defined by the user. These search criteria leverage the features retrieved during analysis to filter through the areas of interest (AOIs) contained in cellrafts. The definition of which AOIs qualify as "good" is determined by the search criteria. After defining the search criteria for a Population, the software will filter through all AOIs found during a scan, keep all the AOIs that pass the search criteria, then return all cellrafts that contain one of these AOIs that pass the filter set.

The Venn Diagram tool allows the users to then further leverage the Populations built in CellRaft Cytometry to conduct analysis across time points. If a CytoSort Array is scanned multiple times, Populations with different search criteria can be defined for each scan. Then, using the Venn Diagram, the intersection, union, symmetric difference, or difference can be retrieved from these populations. For example, the intersection of a Population of cellrafts containing single cells on time point 1 and a Population of cellrafts containing cell colonies on time point 2 would yield a list of all cellrafts that contain a clonal colony of cells that started from single cells.

Display of cellrafts contained in either a Population or the result of using the Venn Diagram can be viewed using the GUI in CellRaft Cytometry. This allows users to rapidly review the output of their search criteria and adjust as necessary. Visuals and readouts on how the image processing algorithms are performing, how many cellrafts are retrieved during querying, and general information on final Venn Diagram set queries can all be provided to the user as well.

Figure 16A:
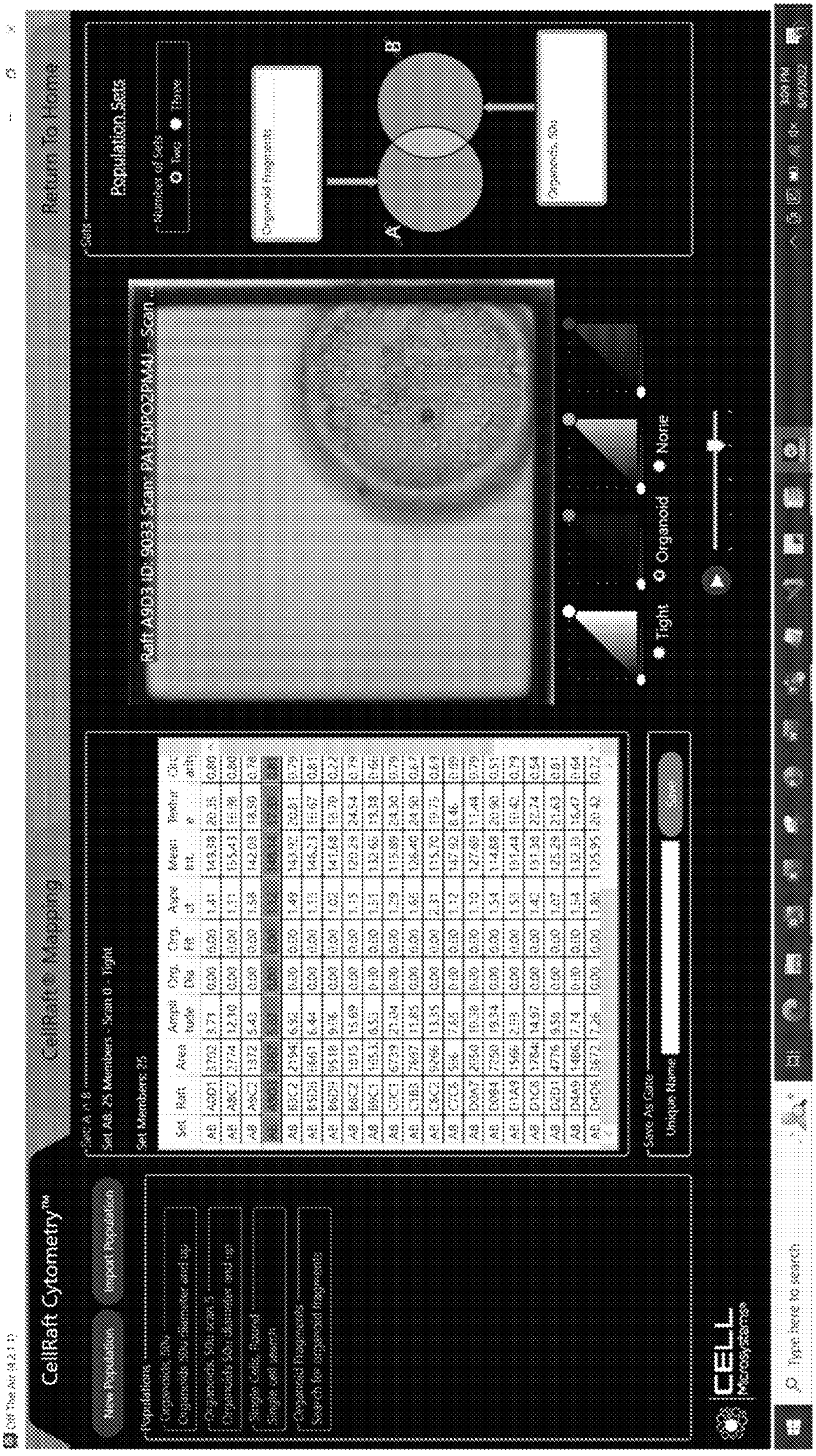
FIG. 16A is a screen shot of an example user interface.

FIG. 16A is a screen shot of an example user interface for the system. The user interface can be displayed, for example, on the computer system 102 of FIG. 2A.

The user interface includes a tab labelled "CellRaft Cytometry™" for providing input and output to the system to query analysis data retrieved during scanning. The user interface includes buttons for creating a new population and importing a population and a window for listing populations. The user interface includes a window for displaying set members and a window for displaying images captured during scanning. The user interface includes a window for displaying population sets.

Figure 16B:
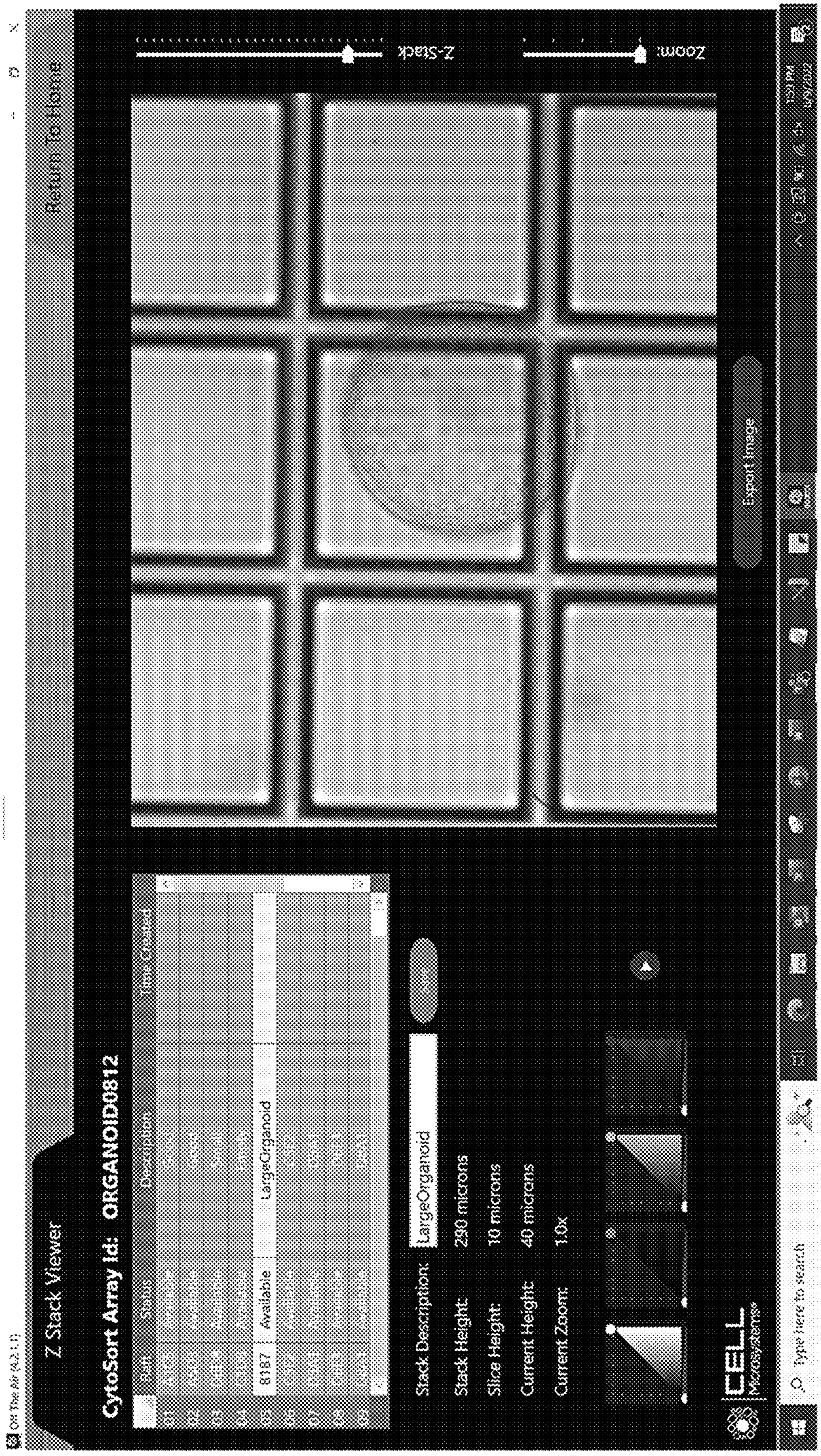
FIG. 16B is a screen shot of another example user interface.

FIG. 16B is a screen shot of an example user interface for the system. The user interface can be displayed, for example, on the computer system 102 of FIG. 2A.

The user interface includes a tab labelled "Z Stack Viewer" for displaying results from query analysis and corresponding images captured during scanning. The user interface provides text fields for descriptions of rafts and descriptions of stacks. The descriptions can be used to cause the user interface to display images of corresponding images. The user interface can include a user interface element, e.g., a slider, for selecting a zoom level for the images.

Figure 16C:
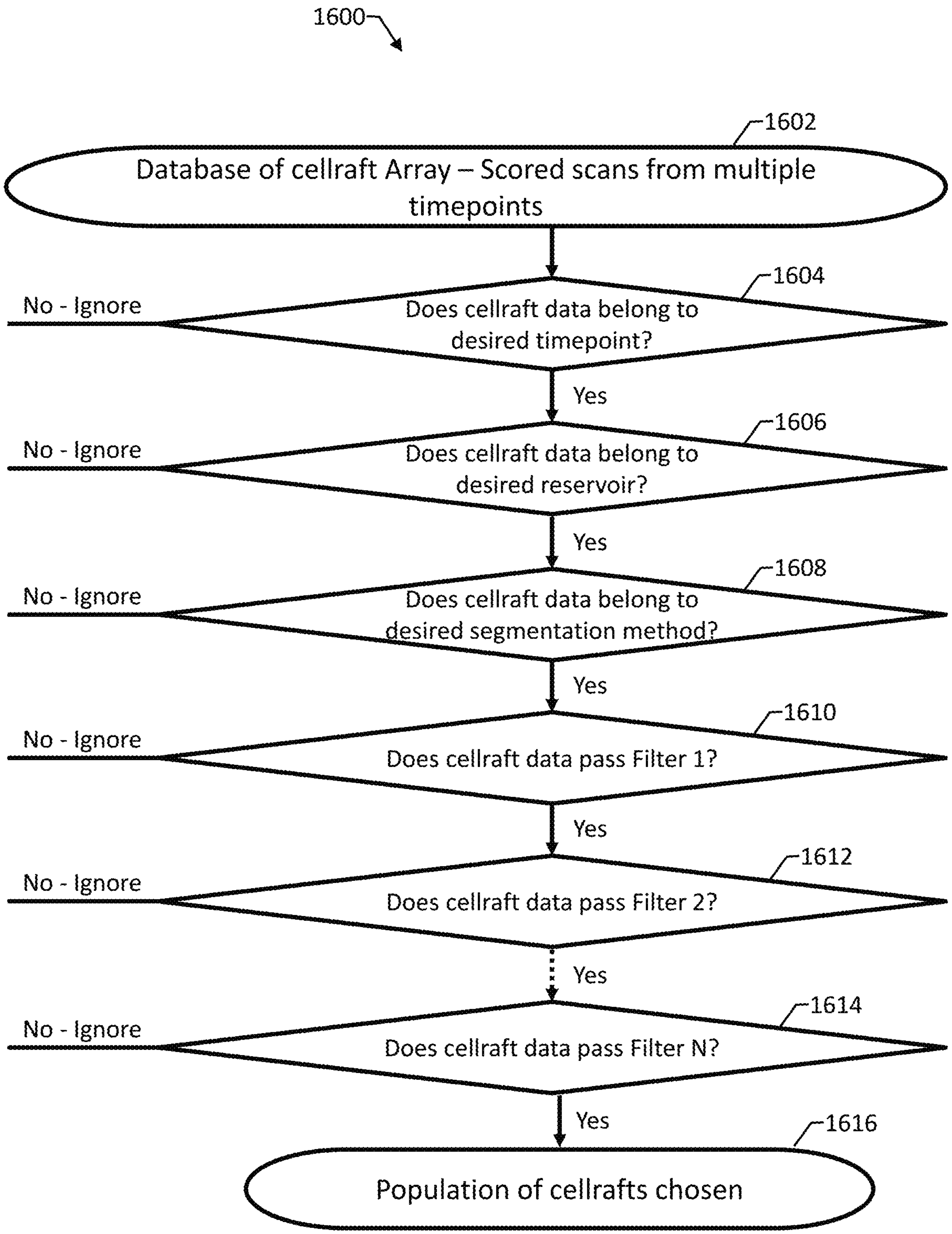
FIG. 16C is a flow diagram of an example method for creation of a population.

FIG. 16C is a flow diagram of an example method 1600 for creation of a population, e.g., using the VennDiagram function. The method 1600 can be performed, e.g., by software executing on the computer system 102 of FIG. 2A.

The method 1600 includes receiving a query and accessing a database of cellraft arrays, the database including scored scans from multiple time points (1602). The method 1600 includes determining, for a selected cellraft, whether the corresponding cellraft data belongs to a desired timepoint, as specified by a query (1604). The method 1600 includes determining whether the cellraft data belongs to a desired reservoir (1606). The method 1600 includes determining whether the cellraft data belongs to a desired segmentation method (1608).

The method 1600 includes determining whether the cellraft data passes one or more filters, up to N filters. As shown in this example, the method 1600 includes determining whether the cellraft data passes Filter 1 (1610), Filter 2 (1612) and up to Filter N (1614). Examples of filter criteria include the following:

Timepoint
Reservoir (if applicable)
Segmentation type
Area
Debris
Aspect Ratio
Solidity
Circularity
Fluorescent Intensity (RGB)
Amplitude
Texture
Mean Intensity
Fiducial AOIs
Fiducial Rafts
AOI Count
Coverage If the cellraft data belongs as specified by the query, then the cellraft is added to the population (1616). Cellrafts are selected and checked until an end condition is reached and then the population is chosen.

Figure 17:
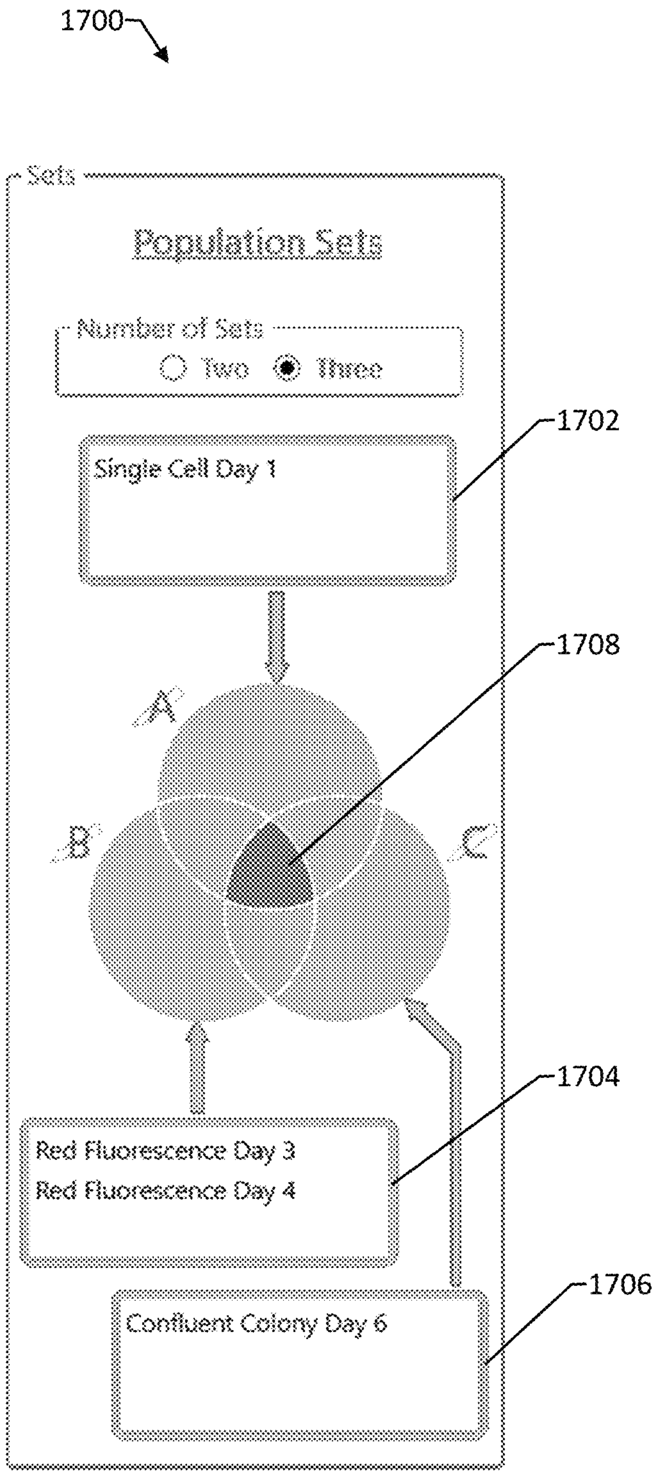
FIG. 17 shows an example user interface for illustrating population sets.

FIG. 17 shows an example user interface 1700 for illustrating population sets. A user can create a set from multiple populations using the user interface 1700. A first user interface element 1702 illustrates Population A-Members of cellraft Population having single cells on day 1 of the experiment. A second user interface element 1704 illustrates Population B—Members of cellraft Population exhibiting target Red Fluorescence on either day 3 or day 4 of the experiment. A third user interface element 1706 illustrates Population C—Members of cellraft Population having of a clonal colony on day 6 of the experiment. A fourth user interface element 1708 shows that the set includes only cellrafts that are members of all three populations A, B and C.

Figure 18:
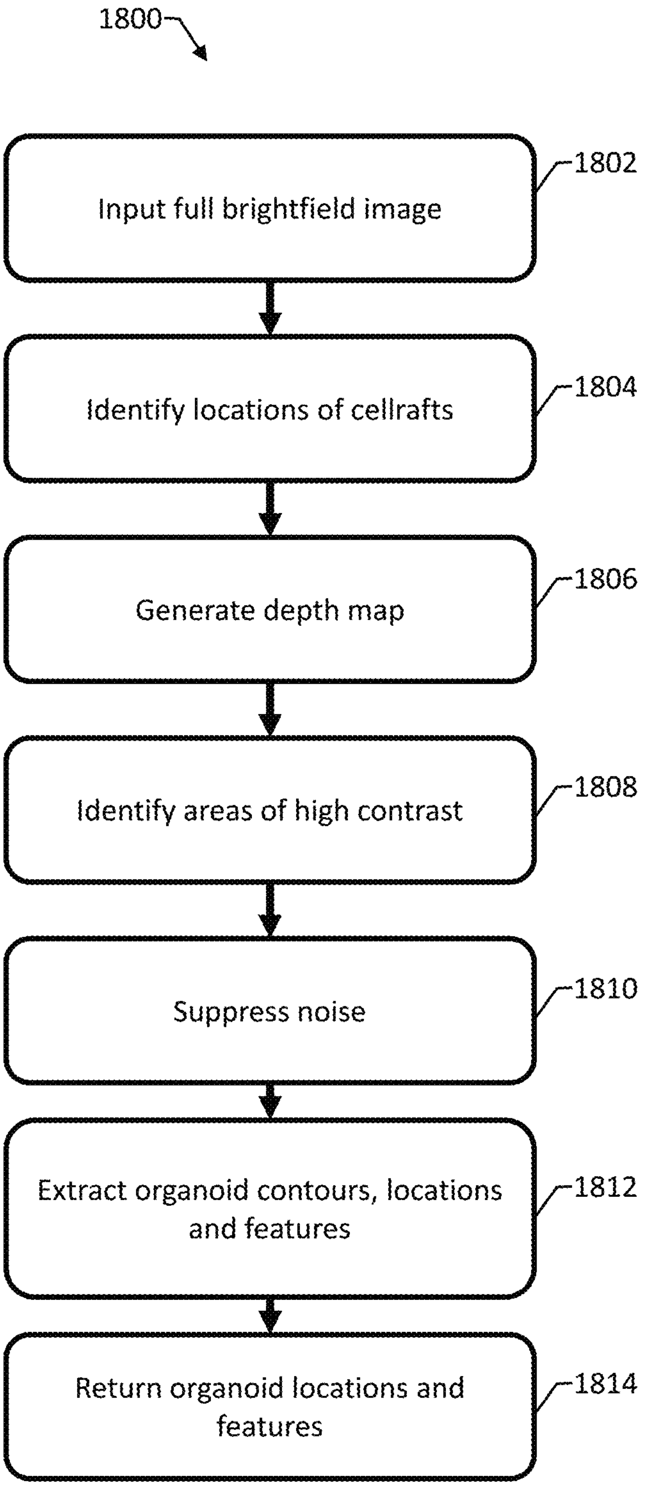
FIG. 18 is a flow diagram of an example method for organoid detection.

FIG. 18 is a flow diagram of an example method 1800 for organoid detection. The system 100 can be configured for detection and selection of organoids of interest in the CytoSort Array. The image analysis algorithms can be configured to allow for users to identify Organoids of specific size. The features and functionality for identifying cell rafts can be applied for organoids, and new parameters can be included for the unique type of analysis that would be done on Organoids and 3D tissue structures. Organoid diameter is the primary feature used to detect organoids of interest; however, several other features that can be used to differentiate between 3-dimensional organoid/tissue growth and 2 dimensional cell growth can be included in the integration of organoid analysis in the system.

The method 1800 can be performed for organoid brightfield segmentation. The method 1800 includes inputting a full brightfield image (1802). The method 1800 includes identifying locations of cellrafts (1804). The method 1800 includes generating a depth map (1806). The method 1800 includes identifying areas of high contrast (1808). The method 1800 includes suppressing noise (1810). The method 1800 includes extracting organoid contours, locations, and features (1812). The method 1800 includes returning organoid locations and features (1814).

Figure 19A:
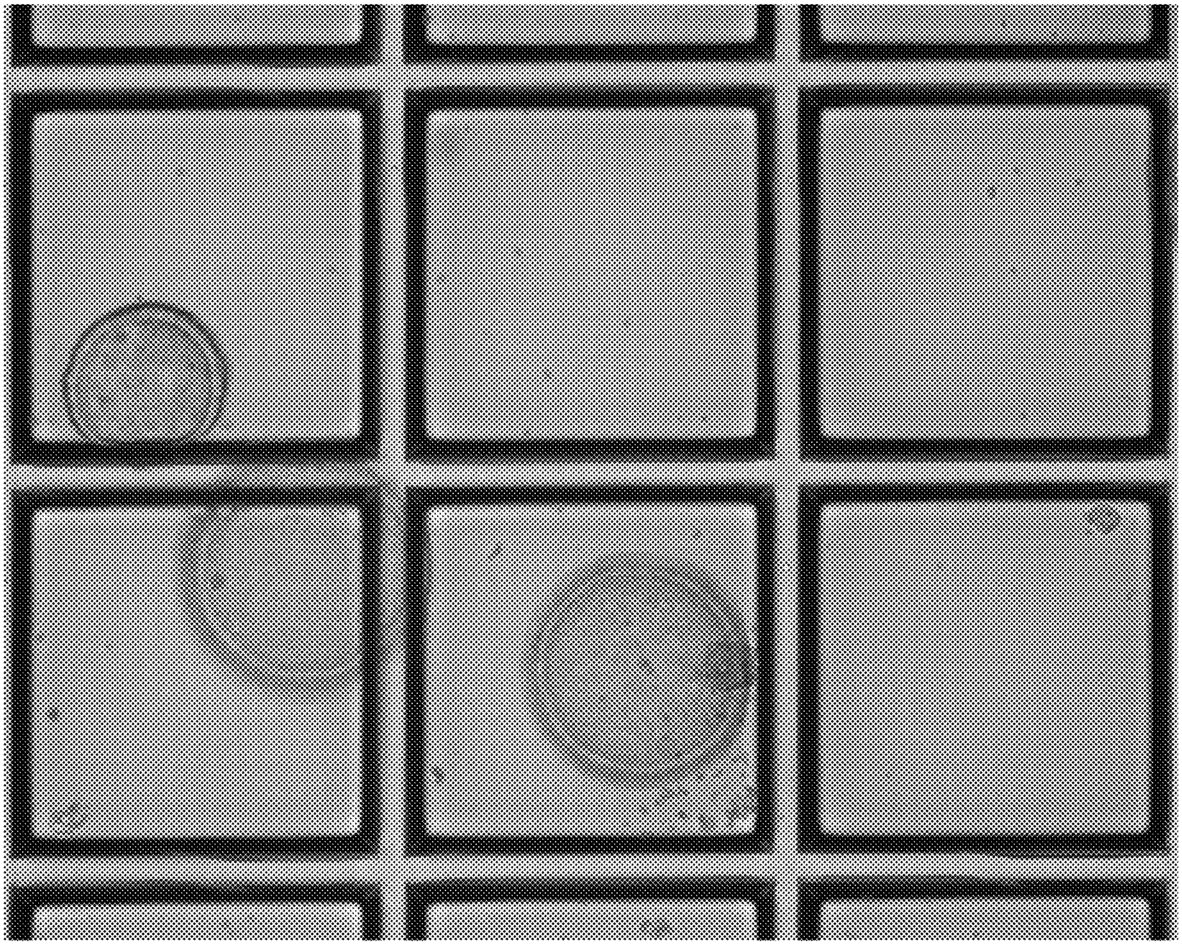
FIGS. 19A-19D show examples of masks and outputs generated by organoid segmentation.
Figure 19B:
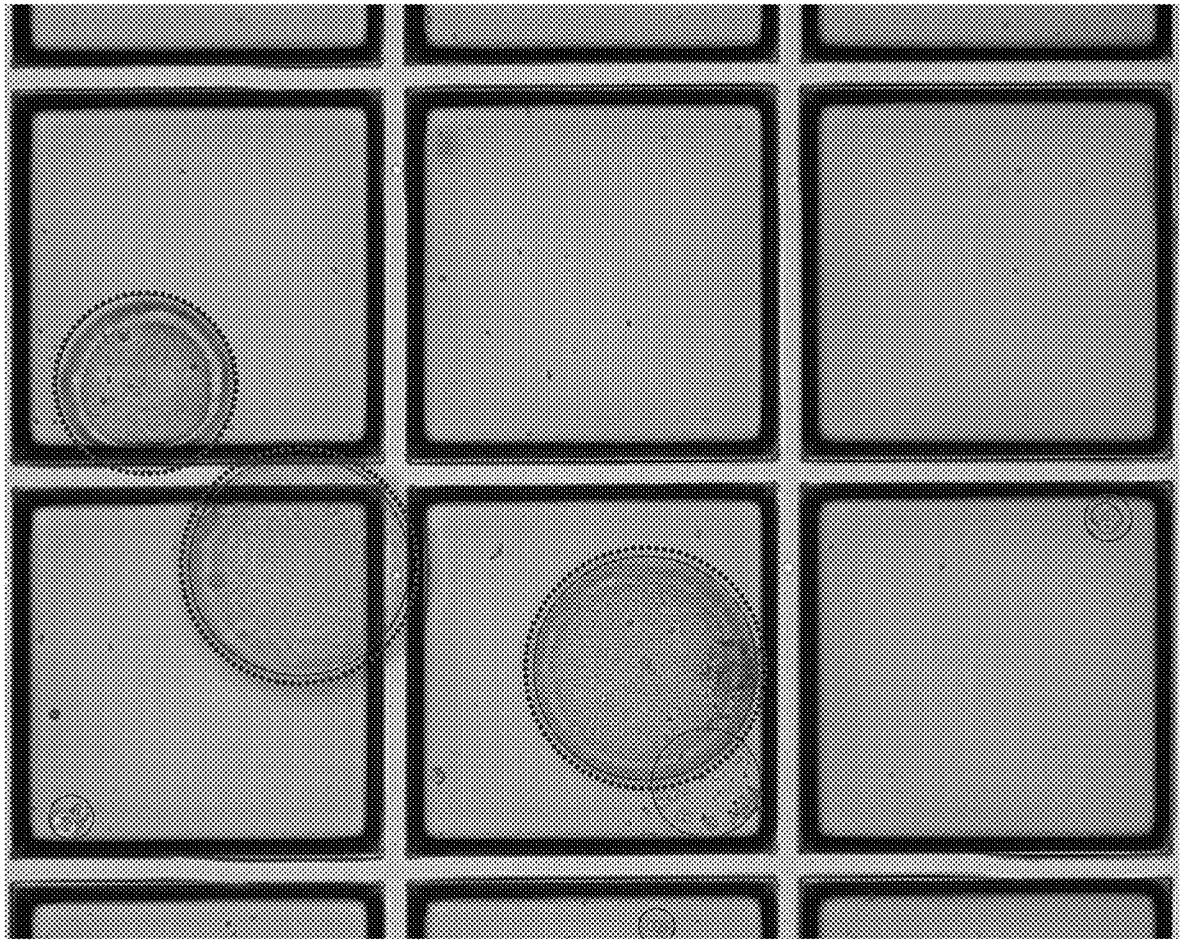
Figure 19C:
Figure 19D:
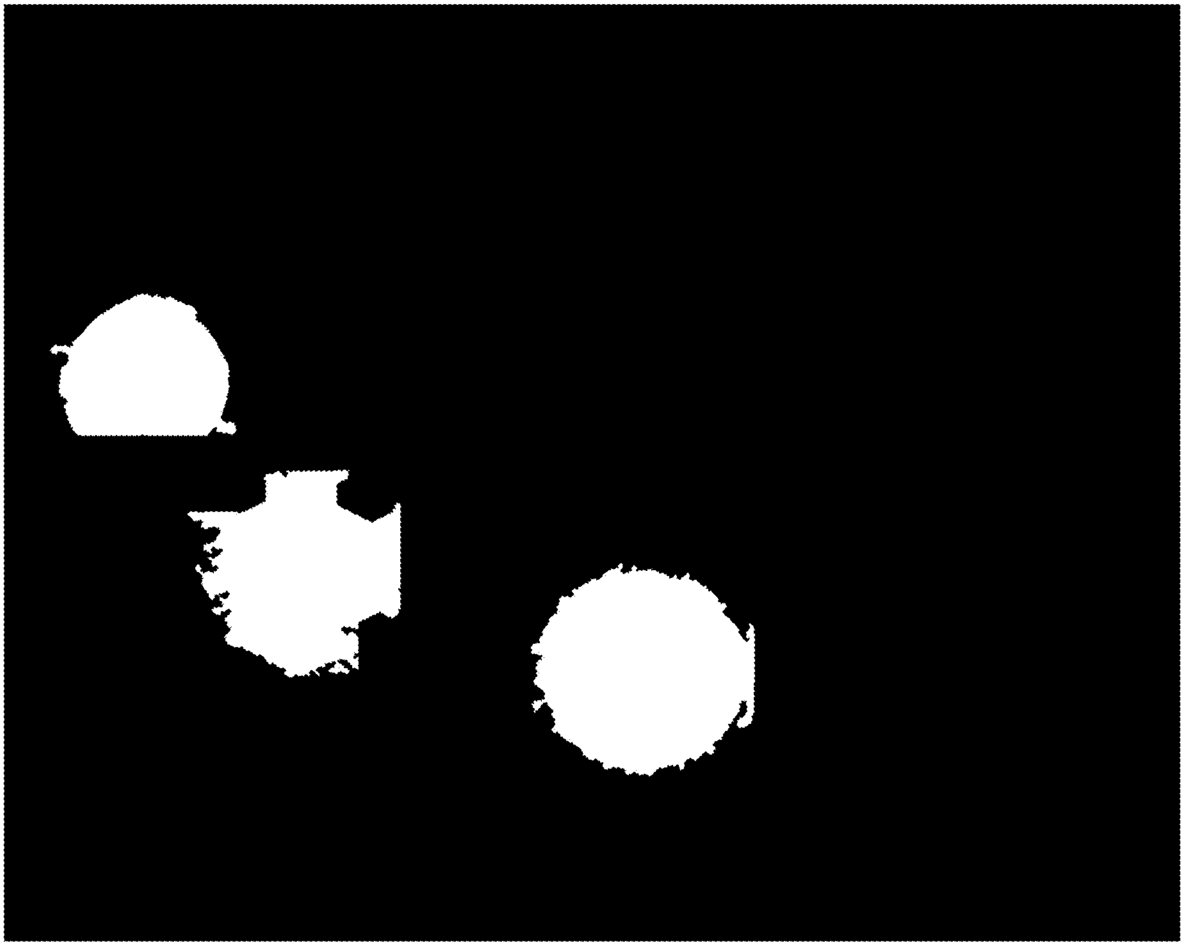

FIGS. 19A-19D show examples of masks and outputs generated by organoid segmentation. FIG. 19A is an example image of cell rafts having organoids. FIG. 19B is an annotated image showing dotted circles around the organoids. FIG. 19C is an example of a mask used for organoid segmentation. FIG. 19D is an example of a different mask used for organoid segmentation.

EXAMPLES

Example 1

Microarray Fabrication

The microarrays were manufactured for organoid culture and recovery utilizing the following protocol. A SU-8 photoresist master template consisting of 80 μm tall, 500×500 μm pillars separated by 30 μm spaces was fabricated by deep reactive-ion etching (Alcatel AMS 100) at the Chapel Hill Analytical and Nanofabrication Laboratory (UNC-Chapel Hill, NC). The master was covalently modified through chemical vapor deposition with octyltrichlorosilane to reduce adhesion to polydimethylsiloxane (PDMS). Sacrificial rigid substrates to ensure efficient dip-coating on the microarrays, as well as minimal PDMS deformity/sag, were prepared by spin-coating (H6-23 Spin Coater, Laurell, North Wales, PA) a thin layer of 7.5% poly(acrylic acid) (PAA) onto glass slides (75×50 mm, Corning, Corning, NY) at 500 rpm for 10 seconds and then 1500 rpm for 30 seconds. PDMS was poured onto the silica master template and degassed for 10 minutes at −710 torr. The master was then placed on the spin-coater for 30 seconds at 225 rpm and then cured at 100° C. for 60 minutes. Demolding the glass-backed PDMS from the silanized master template resulted in a microwell array (80 μm deep, 500×500 μm). Each array was dip-coated in a solution of 20% poly(styrene-co-acrylate) (weight percentage) in gamma butyrolactone (GBL) containing 1% $\gamma Fe_2O_3$ nanoparticles. Polymer solution was isolated in each individual microwell through discontinuous dewetting from the hydrophobic PDMS. Cellrafts were formed after baking off the GBL solvent for 18 hours at 100° C. The cellraft array was bonded to an injection-molded polystyrene cassette using PDMS glue cured at 70° C. for 60 minutes and then oxygen plasma treated (Harrick Plasma, Ithaca, NY) for 2 minutes. Sacrificial glass backings were removed by soaking the backing in DI water at 70° C. for 2 hours to dissolve the PAA. Each array underwent 2 additional minutes of oxygen plasma treatment and then were coated with an anti-bubble solution for 30 minutes. After this treatment, extra solution was aspirated, the array was topped with a polystyrene lid and packaged in a self-sealing sterilization pouch. Completed arrays were then gamma sterilized at 10-15 kGy for 130 minutes (Steris Applied Sterilization Technologies, Libertyville, IL) before use for cell culture.

Array Manufacturing Materials. Sylgard 184 Polydimethylsiloxane (PDMS) was prepared from a silicone elastomer kit from Ellsworth Adhesive Co (Germantown, WI). Octyltrichlorosilane (97%) and gamma butyrolactone were purchased from Sigma-Aldrich (St. Louis, MO). Poly(acrylic acid), 30% solution in water (MW~30 kDa) was purchased from PolySciences, Inc. (Warrington, PA). Custom cassettes were injection molded using polystyrene material and were purchased from Protolabs (Maple Plain, MN). Custom dip-coating solution was prepared at Cell Microsystems, Inc. (Durham, NC).

Example 2

Cell Seeding on the Microarray and Z-Stack Image Acquisition and Analysis

Mouse pancreatic and hepatic organoid suspensions were prepared for cell seeding as fragments from 24-well Matrigel dome culture as described in the manufacturer's protocols (Corning Matrigel Growth Factor Reduced (GFR) Basement Membrane Matrix, Corning, Inc., Corning, NY)) using the standard complete media as described herein below. Mouse hepatic organoids were enzymatically dissociated for single cell suspension using a DNase I with TrypLE solution prepared by mixing 50 μL of 1 mg/mL DNase I Solution (cat #07469, StemCell Technologies, Inc.) with 5 mL TrypLE Express Enzyme (cat #12605010, Gibco Biosciences). Pelleted fragments were resuspended in 1 mL of the DNase I with TrypLE solution for 10 minutes in a 37° C. water bath, mixing the suspension every 2.5 minutes by pipetting to ensure fragments dissociated into single cells. For single cell-derived organoid culture only, complete HepatiCult Growth Medium was supplemented with 10 μM Y-27632 (cat #ACS-3030, ATCC, Baltimore, MD).

Cells, Media, and 3D culture matrix. Mouse pancreatic organoids and mouse hepatic organoids (cat #70933, cat #70932, StemCell Technologies, Inc., Vancouver, BC) were cultured and maintained in a 37° C., 5% $CO_2$ incubator in PancreaCult Organoid Growth Medium (Mouse) or HepatiCult Organoid Growth Medium (Mouse) (cat #06040, cat #06030, StemCell Technologies, Inc.) supplemented with 1% penicillin/streptomycin (cat #15140-122, Gibco Biosciences, Dublin, Ireland) per the manufactures' guidelines for growth and expansion in Matrigel domes (Corning Matrigel Growth Factor Reduced (GFR) Basement Membrane Matrix, Phenol Red-free, LDEV-free, cat #356231, Corning, Inc., Corning, NY).

Cell seeding procedures were adapted from the traditional Matrigel dome culture methods to facilitate seeding within the microwells of the microarray and the release and collection of the cellrafts for single-organoid recovery. To prepare the array for cell seeding, the array was washed three times (3 mL each, 3 minutes per wash) with sterile pre-warmed (37° C.) $Ca^{-}$ $Mg^{-}$ PBS (cat #10010-023, Gibco Biosciences). After the final wash was aspirated, 3 mL of fresh PBS was added to the reservoir and the array was placed on ice for 1 hour to cool the array prior to cell seeding. The organoid fragment or single cell suspension was prepared as previously described. Fragment suspensions were counted by light microscope in n=3 10 µL droplets. Volume needed for seeding the array was calculated using the following equation:

$$\text{Volume needed for seeding } (\mu\text{L}) = \frac{\text{Desired number of fragments}}{(\text{Average fragment count}/10\ \mu\text{L})} \tag{1}$$

For single cell suspension, cells were counted using the Countess II Automated Cell Counter (Invitrogen, Waltham, MA) and volume needed for seeding was calculated by the following equation:

$$\text{Volume needed for seeding (mL)} = \frac{\text{Desired number of cells}}{\text{Cell concentration (cells/mL)}} \tag{2}$$

Cells or cell fragments were seeded at a 1:1 ratio of cells:cellrafts. The desired volume of cell suspension was added to a 15 ml conical tube with 1 mL of cold Advanced DMEM/F-12 (cat #12634010, Gibco Biosciences) and centrifuged at 300×g to pellet the cells. To prepare dilute Matrigel media for cell seeding, the volume of Matrigel needed to achieve a final concentration of 0.24 mg/mL was added to 5 mL ice cold complete PancreaCult or HepatiCult growth media (1.2 mg Matrigel in total seeding volume). After centrifugation, the supernatant was carefully removed, and the cell pellet was resuspended in 1 mL of ice cold dilute Matrigel media. The microarray was removed from ice, PBS was aspirated off the array. To prepare the array for cell seeding, 2 mL of dilute Matrigel media is added to the reservoir, followed by the 1 mL of dilute Matrigel media with cell suspension. After cell inoculation, the remaining 2 mL of cold dilute Matrigel media was slowly added to reach 5 mL total volume within the array reservoir, and the array was returned to ice for 20 minutes. This cold incubation is essential to ensure the dilute Matrigel and cell suspension successfully wick into the microwells prior to polymerization of Matrigel at 37° C. Cells, or clusters of cells, settle into the microwell footprint of the microarray in a Poisson-like distribution and the dilute Matrigel allows for a loose attachment of developing organoids to the cellrafts. After the cold incubation, the array was placed in a 37° C., 5% $CO_2$ incubator. The microarray was scanned in brightfield using the system at 4 hours and every 24 hours after seeding to monitor organoid growth and development.

Live Cell Staining Organoids for phenotypic characterization. Mouse hepatic organoids were stained with Hoechst 33342 (cat #R37605, Molecular Probes, Eugene, OR) and a directly conjugated (FITC) primary antibody for epithelial cell adhesion molecule (EpCAM, cat #11-5791-82, cBioScience, San Diego, CA). Briefly, a 50% media exchange was performed 5 times (2 mL each) using Fluorobrite DMEM (cat #A1896701, Gibco Biosciences) being careful not to dislodge organoids from the microwell footprint. A 2× staining cocktail was prepared as follows: 1.6 mL Fluorobrite DMEM with 400 µL of 10% BSA in PBS (cat #37525, ThermoFisher Scientific, Waltham, MA), 1:400 (20 µL) of the EpCAM primary antibody, 8 drops of Hoeschst 33342. After the final wash with Fluorobrite DMEM, media was removed, leaving approximately 2 mL in the reservoir. The total volume of the staining cocktail was added to the reservoir for a final concentration of 1% BSA, 1:200 EpCAM-FITC primary antibody, and 2 drops per mL Hoechst 33342. The array was placed in a 37° C., 5% $CO_2$ incubator for 45 minutes, followed by five 50% media changes (2 mL each) with Fluorobrite DMEM to wash away excess antibody for imaging. Immediately following staining, the array was scanned using the system in brightfield, blue fluorescence (390/432 nm), and green fluorescence (475/522 nm).

Two organoid-containing cellrafts were selected for additional z-stack imaging with the system, as described herein below. To test the image quality of brightfield and widefield fluorescence z-stacks acquired by the system, two 200-300 µm mouse hepatic organoids on a microarray stained with Hoechst and EpCAM (primary antibody conjugated with FITC) were selected for imaging (as described herein below). Brightfield, blue fluorescence (exposure=50, 50 ms), and green fluorescence (exposure=200, 100 ms) images were acquired every 10 µm across focal ranges that encompassed the full height of the two organoids (24 and 30 images, respectively). The brightfield and false-colored fluorescence images (FIG. 4A) demonstrate excellent image quality with the ability to visualize individual cells, cell junctions (green), and substructures within nuclei (blue), including mitotic figures. The green fluorescence intensity is attenuated toward the top of the organoid, but it is unclear whether that is due to a reduction in excitation-emission light transmission through the lower regions of the organoid, reduction in EpCAM staining, or a combination.

Example 3

System-Acquired High-Quality, Time-Course Images of Developing Organoids

Using both mouse pancreatic (FIG. 4C) and mouse hepatic organoids, a robust and reliable method has been demonstrated for obtaining high-quality, time-course images of developing organoids on the microarray to maintain a dynamic growth record of each organoid during the entire development process from single cell to isolation. Cells were seeded onto the microarray and stained as described herein above. Beginning with a microarray scan shortly after cell seeding (4 hours), the user can identify cellrafts with single or multiple cells either manually or by using a CellRaft Cytometry tool (Cell Microsystems, Inc., Durham, NC) (FIG. 6B). Subsequent serial scans of the microarray were then initiated by the user at desired time intervals to capture temporal images of organoid development (FIG. 6C, FIG. 7). The system was utilized to acquire a full microarray scan in brightfield and three fluorescent channels in under 15 minutes (under 9 minutes for brightfield only), providing a rapid solution for multiparameter phenotypic and morphologic screening of hundreds of individual organoids. In addition to brightfield imaging, the system was used to perform advanced fluorescence-based phenotypic assessment, which can be used for a variety of applications, including live cell staining, CRISPR editing, and on-array viability assays (FIG. 5F). Mouse hepatic organoids stained with FITC-conjugated antibody for EpCAM demonstrated detailed visualization of cell membranes (FIG. 4A, FIG. 7) and Hoechst-stained nuclei enable cell counting throughout the z-stack (FIG. 4A).

Example 4

Isolation of Organoids for Downstream Assays, Growth and Subcloning, and -Omics Applications Using both mouse pancreatic (data not shown) and mouse hepatic organoids, the utility of the disclosed system and methods was evaluated for downstream organoid growth and subcloning, and nucleic acid isolation from individual organoids isolated form the microarray. After isolation from the array into 96-well collection plates, organoids remained viable for downstream assays and continued to grow in dilute Matrigel growth media (FIG. 8A).

The ability to create clonal organoid populations was also demonstrated by leveraging the imaging and isolation capabilities of the presently disclosed system. Organoids derived from single cells were identified as verified by temporal imaging and isolated into 96-well collection plates. After 5 days of growth off-array, each "parent" organoid was enzymatically dissociated in the 96-well plate into small fragments of cells, then re-seeded onto a new microarray to propagate hundreds of second-generation "child" organoids for further expansion or evaluation of lineage-based phenotypes (FIG. 8B).

In addition to performing single organoid isolations for downstream growth, assays, and subcloning, the presently disclosed system was used to automatically deposit single organoids into PCR strip tubes or 96-well PCR plates for nucleic acid isolation, a commonly investigated endpoint for drug discovery and toxicology. Mouse pancreatic (data not shown) and mouse hepatic organoids were seeded onto microarrays and temporal scans were performed to monitor organoid development. Organoids ranging in size from 200 to 700 μm were isolated directly into lysis buffer in standard PCR strip tubes for RNA purification to determine a size threshold for RNA quality and concentration. High-quality RNA (RIN>9.4) was obtained suitable for use in downstream-omics applications (n=8), and the amount of RNA obtained was directly correlated with organoid size (FIG. 9). The data presented demonstrates the flexibility and utility of the disclosed system to provide an all-in-one platform that facilitates efficient, user-friendly workflows for temporal phenotypic assessment of individual organoids upstream of single organoid applications.

RNA purification and quantitation. Individual mouse hepatic organoids ranging in size from approximately 200 μm to 700 μm were isolated using the disclosed system for RNA purification using the Qiagen RNeasy Plus Micro kit (cat #74034, Qiagen, Hilden, Germany). Organoids were released from the microarray and collected using the system's PCR-style wand into PCR strip tubes with 25 μL of RLT Plus Buffer. After isolation was performed, 325 μL of RLT Plus was added to each sample to reach the final volume of 350 μL. RNA purification was performed per the manufacturer's guidelines with a final elution volume of 14 μL. Purified RNA was quantified using the Agilent 2100 Bioanalyzer and RNA 6000 Pico Kit (cat #5067-1513, Agilent Technologies, Santa Clara, CA) using the standard protocol.

Example 5

Generation of CRISPR-Edited Organoids, and Subsequent Clonal Propagation and Functional Screening CRISPR editing is performed on human adult stem cells to introduce a fluorescent reporter. A single cell suspension of the gene-edited stem cells is loaded onto a microarray according to the methods described in Example 2. The cells are cultured in the microarray and monitored at desired time intervals for growth and phenotypic characteristics using the automated system as described above in Examples 3 and 4. Fluorescent CRISPR-edited organoids can be identified using the imaging capabilities of the disclosed system. Organoids of interest are isolated into 96-well collection plates using the automated system for further expansion. After 5 days of growth off-array, each organoid is enzymatically dissociated in the 96-well plate into small fragments of cells, then re-seeded onto a new microarray to propagate hundreds of second-generation reporter organoids. The reporter organoids are screened for pathway activation, differentiation, or phenotypic response to a drug or other molecule.

Cells, Media, and 3D culture matrix. Edited human induced pluripotent stem cells (iPSCs) that express red fluorescent protein (RFP), or green fluorescent protein (GFP) (cat #IPSC1028, cat #IPSC1030, Sigma-Aldrich) were cultured and maintained in a 37° C., 5% $CO_2$ incubator in mTESR Plus (cat #100-0276, StemCell Technologies, Inc.) per the manufactures' guidelines for 2D growth and expansion. To demonstrate iPSC-derived organoid workflows, three commercially available media kits were used to differentiate edited iPSCs into kidney, choroid plexus, and cerebral organoids (cat #05160, cat #100-0824, and cat #08570, StemCell Technologies, Inc.). To grow and monitor phenotypic changes of clonal iPSC-derived organoids, iPSCs were dissociated into a single cell suspension and seeded onto the microarray as described herein above. Dilute Matrigel media (0.24 mg/mL) was made using the manufacturer recommended media for forming kidney, choroid plexus, and cerebral organoids (data not shown). Microarrays were seeded with one edited iPSC cell line, or a mixed population of both RFP and GFP positive cells, to demonstrate the ability to form single color, or dual fluorescent organoids. For differentiation, media changes were performed based on the manufacturers' guidelines for media formulations and duration.

In addition to the ability to generate clonal organoids from single edited iPSCs, the presently disclosed system presents a unique advantage to traditional iPSC-derived organoid culture methods because it enables temporal monitoring of phenotypic changes of individual organoids throughout the differentiation process. Standard techniques for generating iPSC-derived organoids can require moving 3D structures to various culture plate formats, in addition to media changes, to achieve cell differentiation and organoid formation. While they support organoid differentiation, they do not permit assessment of individual structures throughout organoid formation. Using the presently disclosed system, we have demonstrated the ability to generate choroid plexus and kidney organoids from single cells, and small fragments of cells, derived from the same iPSC suspension. Hundreds of single-cell, or fragment-derived, choroid plexus (FIG. 12A) and kidney (FIG. 12B) organoids can be imaged at desired timepoints to closely monitor phenotypic changes throughout the differentiation process.

Figure 13:
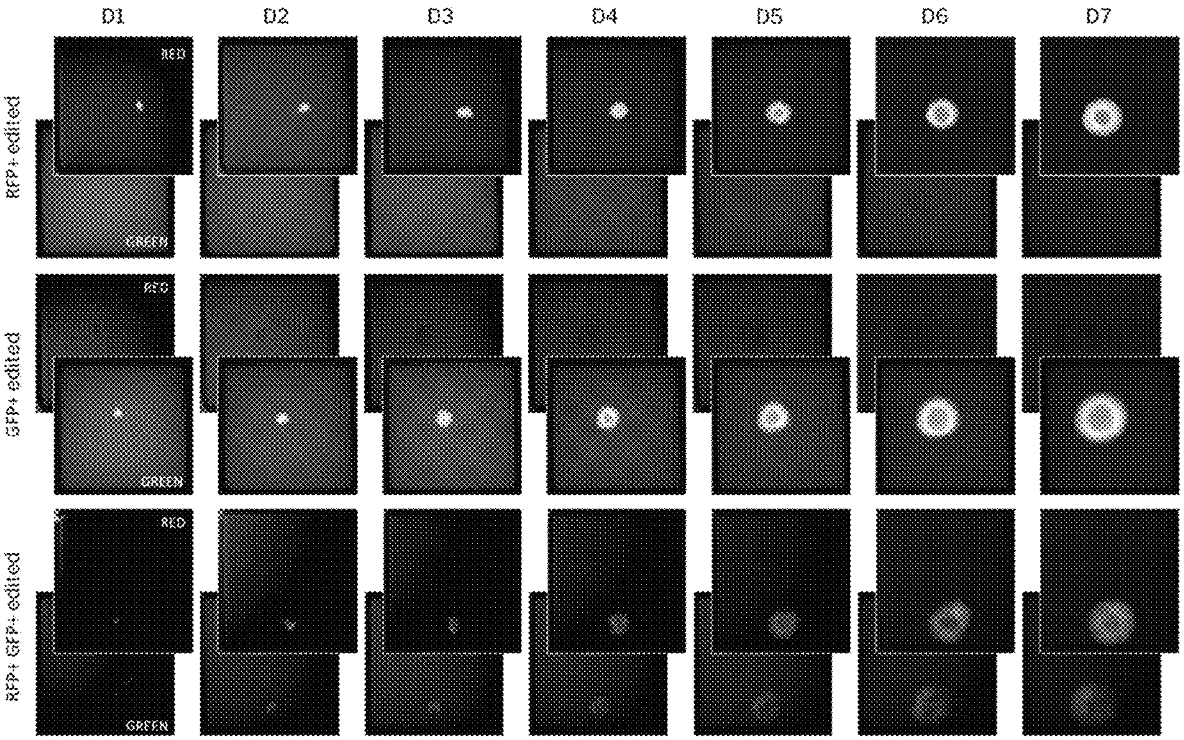
FIG. 13 is a series of images of the microwells of the microarray taken over 7 days illustrating differentiation of RFP+ only, GFP+ only, and both RFP+ GFP+ iPSCs into choroid plexus organoids demonstrating that the system and methods of the present disclosure allows for co-culture of edited iPSCS and a complete data record that can track and trace development of co-cultured pluripotent stem cells to 3D organoids.

Using the presently disclosed system, and methods to seed the microarray described herein above, we have also demonstrated the ability to form dual fluorescent choroid plexus organoids by co-culturing RFP+ and GFP+ iPSCs on the same microarray (FIG. 13). Using the automated system, we can identify cellrafts that contain a single RFP+ iPSC or a single GFP+ iPSC, as well as cellrafts that contain more than one iPSC, of one or both fluorescent reporters. Temporal development of mono- and dual-fluorescent organoids can be monitored and phenotypically characterized, and single organoids can be isolated for further downstream evaluation, including—omics and drug screening applications, or for clonal propagation.

Example 6

Clonal Propagation of Human Tissue-Derived Organoids for Compound-Induced Toxicity Screening A single cell suspension of tissue-specific cells, from common sites of compound-induced toxicity such as liver, kidney, and lung, is loaded onto a microarray according to the methods described in Example 2. The cells are cultured in the microarray and monitored at desired time intervals for growth and phenotypic characteristics using the automated system as described above in Examples 3 and 4. Using the automated system, organoids of interest derived from single cells are identified by temporal imaging and isolated into 96-well collection plates. After 5 days of growth off-array, each "parent" organoid is enzymatically dissociated in the 96-well plate into small fragments of cells, then re-seeded onto a new microarray to propagate hundreds of second-generation "child" organoids. Second-generation clonal organoids, of a desired size range, are isolated using the automated system into 96-well plates for assessment in downstream compound toxicity assays. Clonal, tissue-specific organoids are screened for toxicity to a drug or other molecule for functional response, such as viability, or used for single organoid transcriptomics to reveal cellular mechanisms of toxicity.

Example 7

Custom Organoid Assay Development for Compound-Induced Toxicity Screening Using Single Organoids Using a similar approach to that outlined in Example 6, the automated system described herein above can be used to culture, analyze, and isolate single organoids with similar phenotypic characteristics, including, but not limited to, parameters such as organoid size and morphology, and fluorescent marker inclusion, for reproducible compound-induced toxicity screening assays. To demonstrate a compound-induced toxicity screening assay on single, phenotypically selected organoids, mouse hepatic organoids were grown on the microarray, as described in Example 3. Using the CellRaft Cytometry software described it the presently disclosed system, the population of mouse hepatic organoids were sorted based on organoid diameter. Two populations were selected for isolation; one population for organoids with diameters greater than 50 μm, and a more selective population of organoids ranging from 300-500 μm in diameter. After isolation of cellrafts containing organoids from the populations described above, the 96-well collection plates were spiked with 0.24 mg/mL dilute Matrigel media to support organoid viability and growth post-isolation. Single organoids from each population were treated with a compound with known toxic effects to demonstrate a standard drug-screening assay.

Compounds and Reagents for Toxicity Screening. Mouse hepatic organoids (n=5 per dose) were treated with a five-fold, 6-point dose curve of a canonical hepatotoxicant, acetaminophen (APAP, 0.0008-2.5 mM; cat #A7085, Sigma-Aldrich) in 0.5% dimethylsulfoxide (DMSO, cat #D12345, Molecular Probes). To measure toxicity responses, CellTox Green Cytotoxicity Assay (cat #G8731, Promega Corporation) was used to measure kinetic viability for 72 hours, and CellTiter-Glo 3D Cell Viability Assay (cat #G9681, Promega Corporation) was used to determine the relative viability, via ATP quantitation, at the final 72-hour timepoint.

Figure 14A:
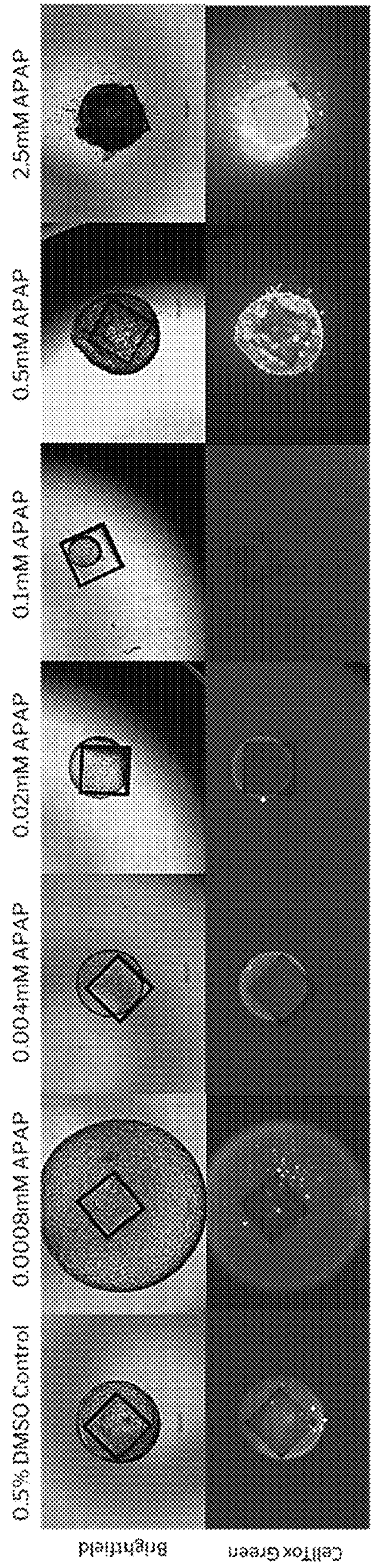
FIG. 14A is a schematic of images showing that organoids, cultured, analyzed, and isolated using the presently disclosed system that are not selected for size prior to isolation for downstream compound-induced toxicity assays results in a heterogenous population for assessment.
Figure 14B:
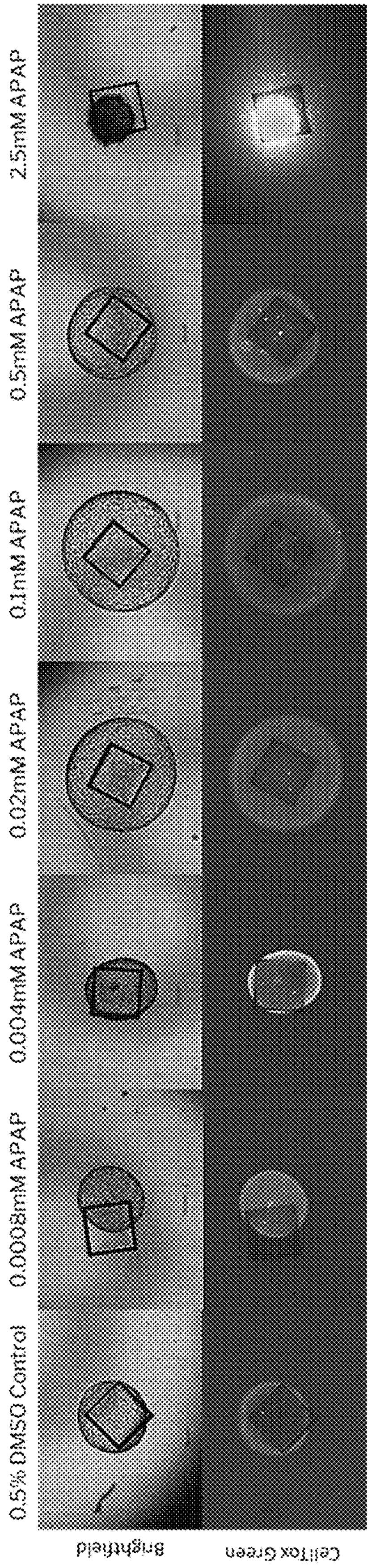
FIG. 14B is a schematic of images showing that the methods presently disclosed for culturing and CellRaft Cytometry can be used to select organoids for isolation based on diameter, which enables customized, single organoid assay development for downstream compound-induced toxicity that maintain inter-assay consistency.
Figure 15A:
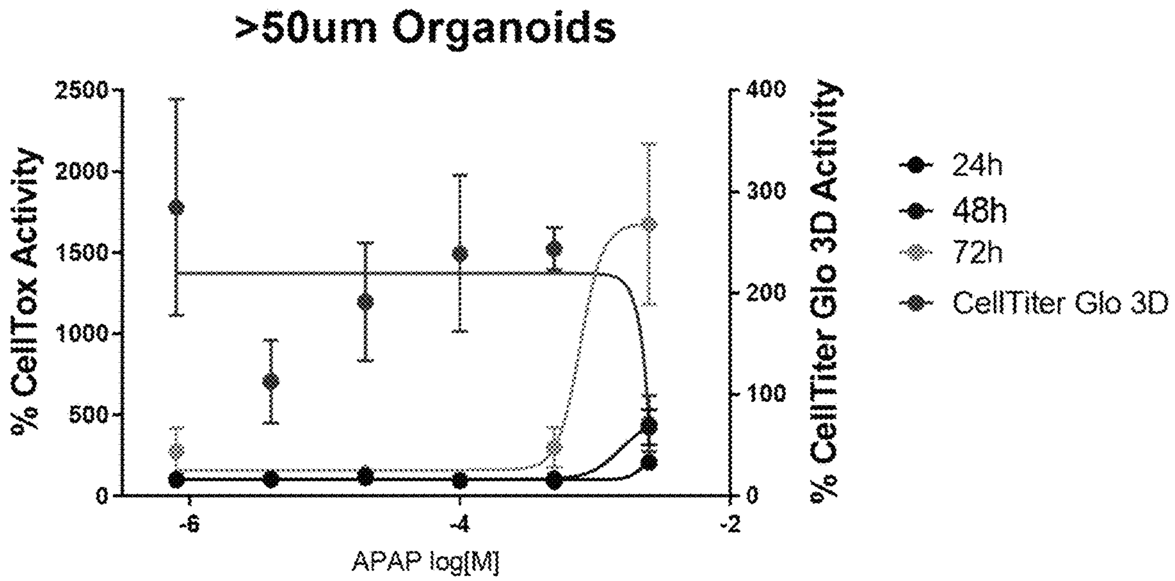
FIG. 15A is a graph demonstrating the system of the present disclosure can be used for growing, analyzing, and isolating single organoids for downstream compound-induced toxicity assays. The graph demonstrates that organoids unselected for size, have large variability in the relative kinetic viability (CellTox Green) and relative terminal ATP (CellTiter Glo) readouts of mouse hepatic organoids treated with a 6-point dose curve (n=5) of acetaminophen (APAP).
Figure 15B:
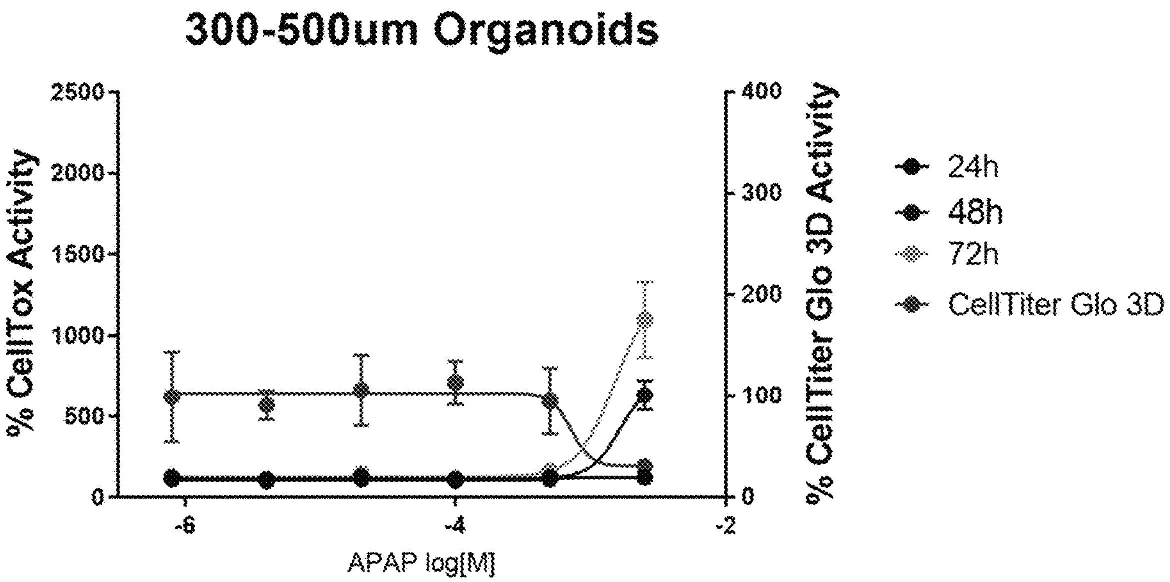
FIG. 15B is a graph demonstrating the system of the present disclosure can be used for building customized, single organoid assays for downstream compound-induced toxicity assays. The graph demonstrates that the automated system can be used to select organoids based on specific sizes to maintain consistency within the assay, which translates to reduced variability in the relative kinetic viability (CellTox Green) and relative terminal ATP (CellTiter Glo) readouts of mouse hepatic organoids treated with a 6-point dose curve (n=5) of acetaminophen (APAP).

Using the presently disclosed system, described herein above, we have demonstrated the ability to generate reliable, reproducible organoid screening assays. Representative images of organoids not selected on size (>50 μm) have a large variability in size (FIG. 14A), whereas organoids that were selected on a more limited diameter range (300-500 μm) maintain more consistent size throughout the assay (FIG. 14B). The ability to select organoids based on size is a critical component in measuring viability readouts, such as CellTox Green and CellTiter-Glo, because these assays are dependent on cell number. The variability in organoid size in the unselected population directly translates to large variability in replicate doses in both viability readouts, which prevents the calculation of an ED50, or mean effective dose (FIG. 15A). Using CellRaft Cytometry to select organoids based on size, organoid size is more consistent, and the viability readouts can be used to calculate an ED50 (0.6003 mM). This approach can also enable assay consistency across many microarrays and 96-well collection plates. In summary, the presently disclosed system presents a unique advantage over traditional methods, which rely on pooled readouts of heterogeneous organoid populations, because assays can be customized to select single organoids based on size, and other phenotypic characteristics, which enables intra- and inter-assay consistency that is unachievable using other methodologies.

Example 8

Propagation of Mono- and Co-Cultured Spheroids for Evaluating Anti-Cancer Therapeutics Spheroids, or tumor cell aggregates, provide a more physiologically relevant in vitro model to study tumor cell responses to genetic manipulations or pharmacological compound effects, making them valuable tools for therapeutic discovery and personalized medicine. A single cell, or aggregate suspension of tumor cells, from human or animal tumors, is loaded onto a microarray according to the methods described in Example 2. The cells are cultured in the microarray and monitored at desired time intervals for growth and phenotypic characteristics using the automated system as described above in Examples 3 and 4. Anti-cancer therapeutics can be added to the microarray, and phenotypic evaluation of the spheroids, such as spheroid size or viability, can be monitored on the array to identify the efficacy of the therapy on the heterogenous spheroid population. Using the automated system, spheroids of interest are identified by temporal imaging and isolated into 96-well collection plates for downstream assessment, such as transcriptomics, as described in Example 4. Alternatively, using the presently disclosed system, spheroids grown on the microarray, as described herein above, can be evaluated using automated CellRaft Cytometry, and isolated into 96-well collection plates for downstream assays of therapeutic agents.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

The invention claimed is:

1. A computer-implemented method, comprising:

obtaining in real-time, using an imaging device, one or more images of one or more cell rafts including one or more cells;

receiving, using at least one processor, the one or more images of the one or more cell rafts including the one or more cells, wherein the one or more images are representative of the one or more cell rafts at least at one of: a predetermined point in time, during a predetermined period of time, and any combination thereof;

processing, using the at least one processor, the one or more images, including:

segmenting the one or more images based on one or more distinct color blobs within the one or more images;

determining that the segmenting was unsuccessful;

generating a histogram of a count of one or more predetermined colors of pixels along at least one axis of the one or more images and identifying one or more boundaries at one or more peaks of the histogram;

generating one or more lines between the one or more boundaries at the one or more peaks of the histogram; and repeating the segmenting of the one or more images subsequent to the generating of the one or more lines until the segmenting is determined to be successful;

extracting, using the at least one processor, one or more features from the one or more processed images in response to a query, the query identifying one or more search criteria;

identifying, using the at least one processor, one or more areas of interest defined by the one or more features extracted from the one or more processed images;

filtering, using the at least one processor, using one or more filters, the one or more areas of interest, and identifying at least one cell data associated with at least one cell in the one or more cells using the filtered one or more areas of interest; and generating, using the at least one processor, a graphical representation of the identified at least one cell data and/or the one or more cell rafts based on the repeated segmenting and presenting the graphical representation on a graphical user interface of at least one computing device.

2. The method of claim 1, wherein the one or more images are stored in one or more storage locations, wherein the receiving includes:

querying the one or more storage locations; and retrieving at least one image in the one or more images from the one or more storage locations.

3. The method of claim 1, wherein receiving the one or more images includes:

scanning the one or more cell rafts in a microarray to generate the one or more images.

4. The method of claim 3, further comprising repeating the scanning of the one or more cell rafts;

wherein repeating the scanning of the one or more cell rafts includes defining at least one other search criteria for at least one iteration of the scanning of the one or more cell rafts in a microarray.

5. The method of claim 4, further comprising:

defining a plurality of sets of cell data representative of the one or more cell rafts using the one or more images, the plurality of sets of cell data being identified based on the repeated scanning using at least one of: the at least one or more search criteria, the at least one or more another search criteria, and any combination thereof;

applying at least one logical operation to the plurality of sets of cell data; and generating, based on the applying, at least one set of cell data having at least one cell data meeting at least one parameter of the logical operation.

6. The method of claim 5, wherein the logical operation includes at least one of the following: an intersection, a union, a symmetric difference, a difference, and any combination thereof.

7. The method of claim 1, wherein the predetermined period of time includes at least one of the following: a plurality of times at which at least one image in the one or more images is obtained, a continuous time interval during which at least a portion of the one or more images is obtained, and any combination thereof.

8. The method of claim 1, wherein the one or more filters include at least one of the following: the predetermined point in time, the predetermined period of time, a type of segmentation of the one or more cells, an area of growth of the one or more cells, debris, an aspect ratio of the one or more images, a solidity, a circularity, a fluorescent intensity, an amplitude, a texture, a mean intensity, one or more fiducial areas of interest, one or more fiducial rafts, one or more area of interest counts, a coverage, and any combinations thereof.

9. The method of claim 1, wherein the one or more images include at least one of the following: a brightfield image of the one or more cell rafts including the one or more cells, a blue fluorescence image of the one or more cell rafts including the one or more cells, a green fluorescence image of the one or more cell rafts including the one or more cells, a red fluorescence image of the one or more cell rafts including the one or more cells, a false-colored fluorescence image of the one or more cell rafts including the one or more cells and any combination thereof.

10. A system, comprising:

an imaging device to obtain in real-time one or more images of one or more cell rafts including one or more cells;

at least one processing circuitry; and at least one non-transitory storage media storing instructions, that when executed by the at least one processing circuitry, cause the at least one processing circuitry to:

process the one or more images of the one or more cell rafts including the one or more cells, the at least one processing circuitry to:

receive the one or more images of the one or more cell rafts from the imaging device;

segment the one or more images based on one or more distinct color blobs within the one or more images:

determine that segmentation was unsuccessful;

generate a histogram of a count of one or more predetermined colors of pixels along at least one axis of the one or more images and identifying one or more boundaries at one or more peaks of the histogram;

generate one or more lines between the one or more boundaries at the one or more peaks of the histogram; and repeat segmentation of the one or more images subsequent to the generating of the one or more lines;

extract one or more features from the one or more processed images in response to a query identifying one or more search criteria, the one or more processed images are of the one or more cell rafts including the one or more cells and are representative of the one or more cell rafts at least at one of: a predetermined point in time, during a predetermined period of time, and any combination thereof;

filter, using one or more filters, one or more areas of interest defined by the one or more features extracted from the one or more processed images, and identify at least one cell data associated with at least one cell in the one or more cells using the filtered one or more areas of interest; and generate a graphical representation of the identified at least one cell data and/or the one or more cell rafts based on the repeated segmenting and present the graphical representation on a graphical user interface of at least one computing device.

11. The system of claim 10, wherein the one or more images are stored in one or more storage locations, wherein the at least one processing circuitry is further to:

query the one or more storage locations; and retrieve the one or more images from the one or more storage locations.

12. The system of claim 10, wherein the imaging device is further to scan the one or more cell rafts to generate the one or more images.

13. The system of claim 12, wherein the imaging device is to repeatedly scan of the one or more cell rafts;

wherein the at least one processing circuitry is to define at least one other search criteria for at least one iteration of the scanning of the one or more cell rafts.

14. The system of claim 13, wherein the at least one processing circuitry is to:

define a plurality of sets of cell data representative of the one or more cells using the one or more images, the plurality of sets of cell data being identified based on the repeated scanning using at least one of: the at least one or more search criteria, the at least one other search criteria, and any combination thereof;

apply at least one logical operation to the plurality of sets of cell data; and generate, from the plurality of sets of cell data with the at least one logical operation applied, at least one set of cell data having at least one cell data meeting at least one parameter of the logical operation.

15. The system of claim 14, wherein the logical operation includes at least one of the following: an intersection, a union, a symmetric difference, a difference, and any combination thereof.

16. The system of claim 10, wherein the predetermined period of time includes at least one of the following: a plurality of times at which at least one image in the one or more images is obtained, a continuous time interval during which at least a portion of the one or more images is obtained, and any combination thereof.

17. The system of claim 10, wherein the one or more filters include at least one of the following: the predetermined point in time, the predetermined period of time, a type of segmentation of the one or more cells, an area of growth of the one or more cells, debris, an aspect ratio of the one or more images, a solidity, a circularity, a fluorescent intensity, an amplitude, a texture, a mean intensity, one or more fiducial areas of interest, one or more fiducial rafts, one or more area of interest counts, a coverage, and any combinations thereof.

18. A computer program product comprising a non-transitory machine-readable medium storing instructions that, when executed by at least one processing circuit, cause the at least one processing circuit to perform operations comprising:

obtaining in real-time, using an imaging device, one or more images of one or more cell rafts including one or more cells;

receiving the one or more images of the one or more cell rafts including the one or more cells;

processing the one or more images, including:

segmenting the one or more images based on one or more distinct color blobs within the one or more images;

determining that the segmenting was unsuccessful;

generating a histogram of a count of one or more predetermined colors of pixels along at least one axis of the one or more images and identifying one or more boundaries at one or more peaks of the histogram;

generating one or more lines between the one or more boundaries at the one or more peaks of the histogram; and repeating the segmenting of the one or more images subsequent to the generating of the one or more lines until the segmenting is determined to be successful;

extracting one or more features from the one or more processed images based on one or more search criteria;

filtering, using one or more filters, the one or more processed images, and identifying at least one cell data associated with at least one cell in the one or more cells using the filtered one or more images; and generating a graphical representation of the identified at least one cell data and/or the one or more cell rafts based on the repeated segmenting and presenting the graphical representation on a graphical user interface of at least one computing device.

19. The computer program product of claim 18, wherein the one or more images are representative of the one or more cell rafts at least one of: a predetermined point in time, during a predetermined period of time, and any combination thereof.

* * * * *